(12) United States Patent
Beck

(10) Patent No.: US 11,400,244 B2
(45) Date of Patent: Aug. 2, 2022

(54) NASAL DEVICE FOR TREATMENT

(71) Applicant: Beck Medical, Ltd., Giva'at Ada (IL)

(72) Inventor: Adva Beck, Giva'at Ada (IL)

(73) Assignee: Beck Medical, Ltd.

( * ) Notice: Subject to any disclaimer, the term of this patent is extended or adjusted under 35 U.S.C. 154(b) by 619 days.

(21) Appl. No.: 16/165,065

(22) Filed: Oct. 19, 2018

(65) Prior Publication Data

US 2019/0314588 A1    Oct. 17, 2019

Related U.S. Application Data

(60) Provisional application No. 62/575,217, filed on Oct. 20, 2017.

(51) Int. Cl.
*A61M 15/08* (2006.01)
*A61F 5/08* (2006.01)
(Continued)

(52) U.S. Cl.
CPC ............. *A61M 15/08* (2013.01); *A61F 5/08* (2013.01); *A61K 9/0043* (2013.01); *A61M 16/06* (2013.01); *A61M 2210/0618* (2013.01)

(58) Field of Classification Search
CPC ............. A24F 47/00; A61B 17/12031; A61B 17/1204; A61B 17/12045; A61B 17/12099; A61B 17/12104; A61B 17/12136; A61B 17/12159; A61B 17/12181; A61B 17/24; A61B 2017/12127; A61F 5/08; A61F 5/56; A61K 31/445; A61K 33/00; A61K 9/0043; A61M 11/00; A61M 11/007; A61M 11/008; A61M 11/02; A61M 13/003; A61M 15/08; A61M 15/085; A61M 16/0459; A61M 16/0461; A61M 16/0479; A61M 16/0486; A61M 16/0666; A61M 16/0672; A61M 16/12; A61M 2016/0039;
(Continued)

(56) References Cited

U.S. PATENT DOCUMENTS 3,568,678 A * 3/1971 Pourquier ............. A61M 31/00
                                                       604/174
3,903,893 A * 9/1975 Scheer ............. A61B 17/12104
                                                       606/196
(Continued)

FOREIGN PATENT DOCUMENTS

CN    204709586 U    10/2015

OTHER PUBLICATIONS

Aschenbrenner et al., "The Influence of Olfactory Loss on Dietary Behaviors", The Laryngoscope, 2008, pp. 135-144, vol. 118.
(Continued)

*Primary Examiner* — Annette Dixon
(74) *Attorney, Agent, or Firm* — The Webb Law Firm

(57) ABSTRACT

Herein disclosed are nasal inserts for treatment and/or management of various different ailments. Easy modification of the insert allows for treatment of various ailments that can readily be treated via the nose. The insert can direct air into or out of the nasal cavity and/or deliver medicinal substances and/or non-medicinal substances to the appropriate regions, thereby providing the appropriate therapeutic effect, depending on the ailment being treated.

48 Claims, 22 Drawing Sheets

(51) Int. Cl.
*A61K 9/00* (2006.01)
*A61M 16/06* (2006.01)

(58) Field of Classification Search
CPC .... A61M 2016/1035; A61M 2025/105; A61M 2037/0023; A61M 2037/003; A61M 2202/0241; A61M 2202/0275; A61M 2207/00; A61M 2210/0618; A61M 2210/0681; A61M 2230/005; A61M 25/10; A61M 31/00; A61M 37/0015; A61M 5/00; A61M 5/3286; B05B 1/14; B05B 11/0035
See application file for complete search history.

(56) References Cited

U.S. PATENT DOCUMENTS

| | | | |
|---|---|---|---|
| 4,886,493 A * | 12/1989 | Yee | A61M 11/00 604/516 |
| 5,601,594 A | 2/1997 | Best | |
| 6,491,940 B1 * | 12/2002 | Levin | A61K 31/445 424/434 |
| 7,730,888 B2 * | 6/2010 | Dunlap | A61M 16/0461 128/207.18 |
| 8,025,635 B2 | 9/2011 | Eaton et al. | |
| 8,517,026 B2 * | 8/2013 | Amon | A61M 15/085 128/207.18 |
| 8,517,029 B2 | 8/2013 | Nelissen | |
| 8,839,790 B2 * | 9/2014 | Beck Arnon | A61F 5/56 128/207.11 |
| 9,265,922 B2 * | 2/2016 | Barbut | A61B 17/12136 |
| 2004/0020492 A1 | 2/2004 | Dubrul et al. | |
| 2005/0240147 A1 * | 10/2005 | Makower | A61B 17/3201 604/96.01 |
| 2009/0248057 A1 * | 10/2009 | Kotler | A61M 16/0666 606/199 |
| 2009/0248058 A1 * | 10/2009 | Kotler | A61F 5/08 606/199 |
| 2010/0030187 A1 * | 2/2010 | Xia | A61M 11/00 604/514 |
| 2013/0085472 A1 * | 4/2013 | Shaari | A61M 5/3286 604/506 |
| 2015/0068537 A1 | 3/2015 | Beck | |
| 2015/0297846 A1 * | 10/2015 | Given | A61K 31/4468 128/200.14 |
| 2017/0157369 A1 * | 6/2017 | Faith | A61M 16/0497 |
| 2018/0256867 A1 * | 9/2018 | Levin | A61M 11/008 |
| 2018/0369007 A1 | 12/2018 | Beck | |

OTHER PUBLICATIONS

Beck Medical, Design U.S. Appl. No. 29/616,909, filed Nov. 21, 2017.

* cited by examiner

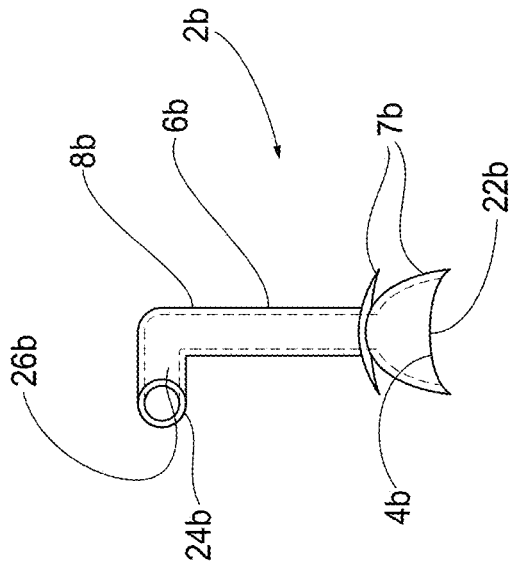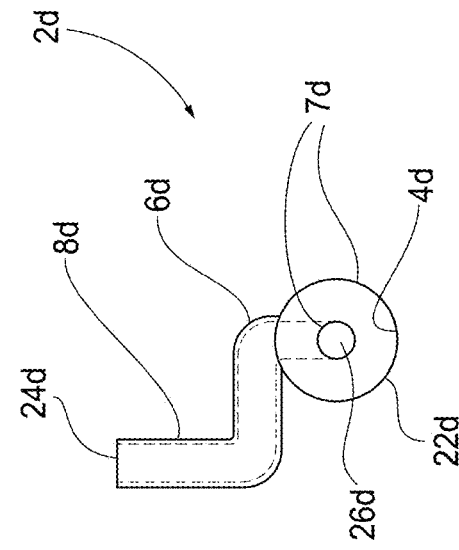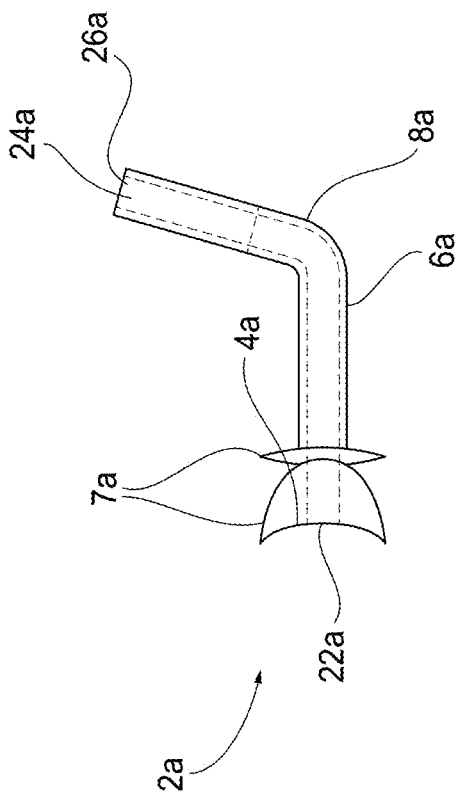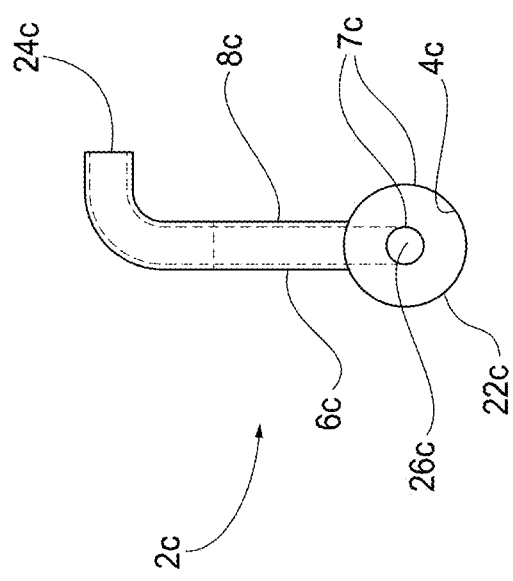
FIG. 2
FIG. 3
FIG. 4
FIG. 5

NASAL DEVICE FOR TREATMENT

CROSS-REFERENCE TO RELATED APPLICATION

This application claims the benefit of U.S. Provisional Patent Application No. 62/575,217 entitled "Nasal Device for Treatment" filed Oct. 20, 2017, which is incorporated herein by reference.

BACKGROUND OF THE INVENTION

Field of the Invention

The present invention relates generally to nasal insert devices and, more particularly, to apparatuses for non-medical and medical treatments and other uses, such as: addiction rehabilitation, brain dementias of many types and other brain related conditions, diabetes, metabolic related illnesses, allergies, migraines, CNS related diseases, and many other uses implemented via nasal insert.

The uses conducted by such apparatuses in different methods, may affect a person's, or other mammal's, physical-, medical-, cognitive-, emotional- and/or other aspects of well-being, by delivering treatments such as for example (not limited to): drug(s), odor(s), other material(s), signal(s) or other which may or may not be environmental, to or through the nasal cavity, or to specific area(s) within the nasal cavity or that is accessible via the nasal cavity. The apparatuses provided herein may also function by preventing particular material(s), signal(s), molecule(s), peptide(s), etc. from either specific area(s) within the nasal cavity or even from reaching the nasal cavity lining entirely or from reaching an area/element via nasal cavity. The apparatuses and methods provided herein may also influence nasal activity in some other manners, for example, in one non-limiting instance by cleaning or removing unwanted material, tissue etc. In another example, by delivering drug(s)/substance(s)/signal(s) etc. to a specific destination in the superior meatus (or other location). In other non-limiting examples, by manipulating the olfactory or the olfactory region and/or other intra-nasal areas. Such manipulation may include, for example (without limitation), things like: affecting: hormones, receptors, processes, brain activity, odors/odors perception, signaling and/or neural activity; delivering: drug, odor, substance, peptide, signal bacteria, treatment etc. In addition the apparatuses of the current invention may act, by leveraging specific nasal characteristics, for example, affecting and/or reaching other areas of the body through acting over or via the connection between the nose to other parts of the body, such as the brain, endocrine system, lungs, throat, or blood system. In another example, by manipulating, and/or guiding, some environmental elements such as an odor, air, air-borne element, etc., through the nasal cavity to deliver a treatment, or for any other suitable use.

Background of the Invention

The nasal structure is unique and complex. It starts with the nostril opening and is followed by the nostril vestibule. The forward section, within and above each nostril, is called the vestibule. Behind the vestibule there is the nasal valve which is a dynamic narrow element, and further deeper along the lateral wall are three elevations, running generally from front to rear. Each elevation, called a nasal concha or turbinate, hangs over an air passage. These air passages are also known as the inferior meatus—the largest, the middle meatus, the posterior meatus and the superior meatus which is the smallest, upper most passage. The upper most meatus provides access to several elements such as, part of the sinuses, as well as the olfactory region which has been proven to contain receptors for many hormones, and for directly linking the nose and the senses of the nose to several brain functions such as memory, amygdala and branches of the trigeminal nerve that are considered essential for Nose to Brain (N2B) therapy.

The olfactory region has also connectivity to the Central Nervous System (CNS). Due to its location and size, the uppermost concha, is the most difficult to reach to. The middle meatus, which is also difficult to reach, provides access to part of the sinuses opening as well as to other elements. The conches are not connected to the septum, and there exists a passage from the nasal floor to the nasal roof. The majority of the inhaled air naturally flows through the inferior meatus. Another portion of the air goes through the middle one and only minority of the air reaches the upper and superior meatuses.

The nasal cavity due to its physical characteristics, serves as a perfect drug delivery and treatment vehicle. Its mucosa and cilia are rich in blood vessels and enable quick absorption of materials directly to the blood system. The nasal cavity is also connected to the endocrine system and brain through the nasal roof, olfactory region, branches of the trigeminal nerve, blood vessels and through other elements, which allows for direct Nose to Brain (N2B) treatments via specific drug and/or substance delivery, as well as via other manipulations. Nasal based treatments also serve as an excellent alternative for needle injection based therapies and vaccinations, especially for therapies where adverse events in the gastrointestinal tract and first-pass metabolism in the liver are to be avoided.

Although, in theory, the nose appears to be the perfect location for treatment delivery, the mammalian nose is, as discussed above, extremely complex in structure. The complex convoluted nasal cavity anatomy, having the narrow nasal valve, and the routine cyclic change of nasal mucosa is directed to serve well for different need such as: the protection of lungs, the adaptation of the air to the lungs and body, for enabling smelling and olfactory activity etc. It includes for example: filtration, change of air's temperature, moistening, and other acts—conducted in a very short time through the pass of air through the nose. Also through exhalation the nasal conducts several acts over air. However, these anatomical and functional features impose substantial obstacles on nasal drug delivery and often times lead to inefficient treatment or even harmful and damaging side-effects to the nasal cavity or to other parts of the body due to administration to the wrong area or due to other problems, for example: transport of medicine to the lungs instead of to the sinuses.

The most challenging element is to deliver the drug to or to provide the treatment in the exact desired location of the nasal cavity, especially when the required location is located beyond the nasal valve and is located in the middle, upper or superior meatus the upper and superior meatus and to the regions innervated by the olfactory and branches of the trigeminal nerve for efficient "nose-to-brain" (N2B) treatment administration. Additionally, another challenging aspect of nasal treatment delivery to the required location, is minimizing or avoiding such delivery from other areas. For example, not delivering the drug to locations other than to the middle meatus where part of the sinuses openings are located, or to prevent some substance (environmental or other) from contacting the nasal lining/from reaching the blood stream etc.

Accordingly, there is a need in the art and in actual current reality to provide a device or set of devices that may answer such needs and will enhance possibilities for drug delivery and treatment in general via the nasal cavity.

SUMMARY OF THE INVENTION

The apparatuses of this invention, due to their unique characteristics, enable administration of the treatment to specific intranasal areas or to specific areas external to the nasal area while transporting it through the nasal or by leveraging other nasal characteristics, while preventing or reducing the reach of such treatments to unwanted areas, if needed. In particularly the apparatuses described in this invention are suited to manipulate/change/inhibit/initiate and/or control the reach of signals/inputs/molecules etc. to a specific area within the nasal cavity in order to lead to the wish-full reaction for example (not limited): for delivering specific molecule(s)/generating specific signal(s)/excitation of a receptor/the secretion/creation of hormone/signal/peptide/for successful nose to brain drug delivery/and for many other uses.

The apparatuses detailed in this invention may serve for any treatment that can be provided by using them, or for any other use wellness or other done with them. The apparatuses provided herein enable direct and efficient drug delivery, or other material/signal/other delivery, to a specific and desirable area within the nasal cavity or beyond it—for example: the lungs, the sinuses, the brain, CNS, blood stream, or various other areas, etc. (hereinafter: the Target Area, i.e. "TA"). The apparatuses can also function by or for preventing air/drug/specific substances/odors/signals/molecules/ other etc. from entering the nasal cavity or preventing them from reaching to specific area (s) within the nasal cavity or areas that are accessible via the nasal cavity, or directing such thereto. Here are few examples ((non-limiting), for procedures that can be done by using the apparatuses provided herein: delivering a drug or other treatment to its desired location in the superior meatus, manipulating the olfactory senses or olfactory related receptor(s)/signaling/ input(s)/activity(ies)/nerve connectivity, etc., and/or other intranasal regions, leveraging nasal characteristics and/or connectivity to act over other locations/targets in the body, such as the brain, endocrine system, lymphatic system, lungs, throat, blood system etc., or to verify that unwanted substances will not reach them, or manipulating some environmental element such as odor or other airborne elements or other bio-chemical signals, or in-body elements/signals/ etc. elements/signals/etc. from other sources By doing any one of the above, the apparatuses of this invention allow for efficient drug delivery, manipulation over the Target Area within the nasal cavity, and/or the manipulation of nasal cavity components in order to reach Target Areas such as the brain, sinuses, lungs, blood system, etc.

Due to the challenging nature of introducing and/or delivering therapeutic agents via the nasal cavity or conducting manipulation overt nasal cavity parts, or co-acting with it in any manner, there is a need in the art to provide a device or set of devices that may answer such needs and will enhance possibilities for drug delivery and treatment via the nasal cavity.

Therefore, an objective of the present invention is to provide methods relating to the use of intranasal devices for the administration of different therapeutic agents and/or for conducting the required manipulation in order to achieve a relevant affect in the treatment of various ailments or in order to produce the required effect for medical or non-medical uses.

The implementation of such objectives is achieved via a set of threads/branches, pipes, seals, "sheets", membranes/valves/filters, structural elements, materials and other mechanisms structures and technologies that are leveraged for providing the treatment and to directing it and/or preventing it and in generally for achieving the desired result(s).

More specifically, provided herein, is a nasal insert for insertion into a nasal cavity including a body having an inner surface defining a first air passageway and an outer surface, the body having a first end, a second end, wherein the body extends along a non-linear path to direct incoming air to a specific region of the nasal cavity through the first air passageway.

Any of the nasal inserts provided herein, wherein the non-linear path includes a curved portion.

Any of the nasal inserts provided herein, wherein the non-linear path includes a plurality of segments extending in different directions.

Any of the nasal inserts provided herein, wherein adjacent segments are substantially transverse to each other.

Any of the nasal inserts provided herein, wherein the body further includes a second air passageway in fluid communication to the first passageway wherein the body has a third end, the first end corresponds to a proximate end and the second end and third end correspond to respective distal ends of the first passageway and the second passageway where the first end is adapted to be positioned closer to the entrance of a person's nostril than the second end or third end.

Any of the nasal inserts provided herein, wherein the nasal insert has a plurality of passageways terminating at a plurality of respective ends.

Any of the nasal inserts provided herein, wherein a unitary thread-like element extends from the outer surface of the body and is positioned between the first end and the second end, wherein the thread-like element includes a medicament.

Any of the nasal inserts provided herein, wherein the valve is defined in the body of the insert and permits gas to flow in one direction through the body, the valve is positioned between the first end and the second end.

Also provided herein is a nasal insert for insertion into the nasal cavity, including a body having an inner surface and an outer surface, the inner surface defining the passageway wherein the passageway for incoming gas and discharge gas has a proximate end for placement in close proximity to an entrance to the nasal cavity and a plurality of distal ends that are positioned away from the proximate end.

Any of the nasal inserts provided herein, wherein incoming and discharging gas can pass through all of the proximate and distal ends.

Any of the nasal inserts provided herein, wherein a valve is provided within the passageway so that gas can only pass in one direction in one of the distal ends.

Any of the nasal inserts provided herein, wherein the body is configured to direct incoming gas exiting to distal ends to specific areas in the nasal cavity.

Any of the nasal inserts provided herein, wherein the outer surface includes a seal extending therefrom configured to coact with a user's nasal cavity to prevent air from passing across the seal.

Any of the nasal inserts provided herein, wherein the outer surface includes a seal extending therefrom to prevent air from passing across the seal.

Any of the nasal inserts provided herein, wherein the outer surface includes a seal extending therefrom and wherein the seal is configured to coact with a user's nasal cavity to fulfill its purpose.

Any of the nasal inserts provided herein, wherein one of the inner surface and the outer surface of the body includes a medicament to be received by a patient.

Any of the nasal inserts provided herein, wherein a thread-like element extends from the outer surface of the body and is positioned between the proximate end and the distal ends, wherein the thread-like element includes a medicament.

Any of the nasal inserts provided herein, wherein the thread-like element is a solid longitudinally extending element that extends from the outer surface of the body.

Any of the nasal inserts provided herein, wherein a plurality of thread-like elements extend from the outer surface of the body.

Any of the nasal inserts provided herein, further including a non-sealable hook extending from the body that holds the insert in place.

Any of the nasal inserts provided herein, wherein an expandable non-sealable leaf having a flat surface extends from the outer surface of the body, wherein the surface of the leaf includes a medicament.

Any of the nasal inserts provided herein, wherein the leaf includes a material that dissolves over time.

Any of the nasal inserts provided herein, further including a valve in communication with the passageway, wherein the valve permits gas to flow in one direction through the passageway.

Any of the nasal inserts provided herein, wherein the valve is a flap that permits gas to flow in one direction through the passageway.

Any of the nasal inserts provided herein, wherein the valve is defined in the body of the insert and permits gas to flow in one direction through the body, the valve is positioned between the proximate end and the distal ends.

Any of the nasal inserts provided herein, further including a non-sealable deflector extending from the body to deflect the flow of gas external to the passageway.

Additionally provided herein is a nasal insert for insertion in a nasal cavity including: a body; a hook attached to the body to hold the body in place; and an expandable flat leaf containing medicament extending from the body, wherein the leaf is not a seal.

Any of the nasal inserts provided herein, wherein the leaf is made of a heat-sensitive material that will dissipate over a period of time.

Any of the nasal inserts provided herein, wherein the body further includes a thread-like element extending from the body, the thread-like element having a medicament.

Any of the nasal inserts provided herein, wherein the thread-like element includes a unitary body.

Any of the nasal inserts provided herein, further including a deflector extending from the body to deflect air passing across the body.

Any of the nasal inserts provided herein, wherein the body includes a passageway configured to direct air over the leaf.

Further provided herein, is a nasal insert for insertion into the nasal cavity including a U-shaped body, the body having an inner surface and an outer surface, the inner surface configured to form a passageway with a surface of the nasal cavity and to permit gas to pass thereby, the outer surface including a seal extending therefrom.

Also provided herein is a nasal insert including a body configured to be inserted into a nasal cavity, and a thread-like element extending from the body having a medicament.

Any of the nasal inserts provided herein, further including a seal attached to the thread-like element.

Any of the nasal inserts provided herein having no hollow passageway.

Any of the nasal inserts provided herein having membrane/s enabling one or multidirectional pass of specific substances/signals and/or blocking specific substances/signals.

Provided herein is a nasal insert for insertion into a nasal cavity comprising a body having an inner surface defining a passageway and an outer surface, wherein the body extends along a path to direct air and/or other components to reach a specific region of the nasal cavity or beyond it, and/or to prevent the reach of air and/or other components from a specific area in the nasal cavity or beyond it or to reduce the amount of air and/or other components in specific areas of the nasal cavity.

Any of the nasal inserts provided herein wherein the path includes a curved portion.

Any of the nasal inserts provided herein, wherein the nasal insert body includes one or a plurality of segments extending from it.

Any of the nasal inserts provided herein, wherein adjacent segments are substantially transverse to each other.

Any of the nasal inserts provided herein, wherein the nasal insert has a plurality of passageways beginning and/or terminating at a plurality of respective ends.

Any of the nasal inserts provided herein, wherein the body includes a seal extending therefrom configured to coact with a user's nasal cavity to prevent air and/or other components from passing across the seal, or wherein the seal is a partial seal or a selective seal thereby reducing the amount or the effect of the air and/or other components.

Any of the nasal inserts provided herein, wherein the body includes a seal extending therefrom configured to prevent air and/or other components from passing across the seal, or wherein the seal is a partial seal or a selective seal thereby reducing the amount or the effect of the air and/or other components.

Any of the nasal inserts provided herein, wherein the body includes a seal extending therefrom and wherein the seal is configured to coact with a user's nasal cavity to fulfill its purpose.

Any of the nasal inserts provided herein, wherein the nasal insert comprises a component able to create a required effect.

Any of the nasal inserts provided herein, wherein a unitary thread-like element extends from the body, wherein the thread-like element includes a component able create a required effect.

Any of the nasal inserts provided herein, wherein the thread-like element is a longitudinally extending element that extends from the body, and wherein the thread-like element does not comprise a passageway therein.

Any of the nasal inserts provided herein, wherein a plurality of thread-like elements extend from the body.

Any of the nasal inserts provided herein, further comprising a hook for holding the insert in place.

Any of the nasal inserts provided herein, wherein an expandable leaf-like element extends from the body, wherein the leaf-like element includes a component able to create the required effect.

Any of the nasal inserts provided herein, wherein the body comprises a component able to create the required effect, wherein the component is delivered over time, in response to a trigger.

Any of the nasal inserts provided herein, wherein the leaf-like element is attached to the body of the nasal insert by thread-like or string-like.spring-like elements, wherein the component able to create the required is present on the thread-like or string-like elements, and wherein the component is delivered over time, in response to a trigger.

Any of the nasal inserts provided herein, further comprising a valve in communication with the passageway, wherein the valve permits air and/or other components in one direction in the passageway.

Any of the nasal inserts provided herein, wherein the valve is defined in the body of the insert thereby permitting air and/or other components in one direction through the body.

Any of the nasal inserts provided herein, further comprising a deflector extending from the body to deflect the flow of air and/or other components external to the passageway.

Also provided herein is a nasal insert for insertion into the nasal cavity, comprising a body having an inner surface and an outer surface, the inner surface defining the passageway wherein the passageway(s) for incoming air and/or other components and discharge air and/or other components has proximate end(s) for placement in close proximity to an entrance to the nasal cavity and a plurality of distal ends.

Any of the nasal inserts provided herein, wherein incoming air and/or other components and discharging air and/or other components can pass through all or through part of the proximate and distal ends.

Any of the nasal inserts provided herein, wherein a valve is provided within a passageway so that the flow of air and/or other components is allowed in one direction in one of the ends.

Any of the nasal inserts provided herein, wherein the body is configured to direct air and/or other components flow to specific areas in the nasal cavity or beyond it.

Any of the nasal inserts provided herein, wherein the body includes a seal extending therefrom configured to coact with a user's nasal cavity to prevent air/components from passing across the seal, or thereby reducing the amount or the effect of the air and/or other components passing across the seal, wherein the seal may serve as a total seal, as a partial seal, or a selective seal.

Any of the nasal inserts provided herein, wherein the body includes a seal extending therefrom configured to prevent air/components from passing across the seal, or thereby reducing the amount or the effect of the air and/or other components passing across the seal, wherein the seal may serve as a total seal, as a partial seal, or a selective seal.

Any of the nasal inserts provided herein, wherein the seal is configured to fulfill its purpose by coacting with a user's nasal cavity.

Any of the nasal inserts provided herein, wherein the inner surface and/or the outer surface of the body and/or any layer in between, or any other part of the nasal insert comprises a component able to create a required effect to a user.

Any of the nasal inserts provided herein, wherein a thread-like element extends from the body, wherein the thread-like element comprises a component able to create a required effect to a user.

Any of the nasal inserts provided herein, wherein the thread-like element is a longitudinally extending element that extends from the body, and wherein the thread-like element does not comprise a passageway therein.

Any of the nasal inserts provided herein, wherein a plurality of thread-like elements extend from any surface of the body.

Any of the nasal inserts provided herein, wherein an expandable leaf-shape having a relatively flat surface extends from the nasal insert body by thread-like or string-like/spring-like elements, wherein the surface of the leaf comprises a component that can produce a required effect to a user.

Any of the nasal inserts provided herein, wherein elements of the nasal insert body comprise a component that is delivered over time and/or in response to some trigger.

Any of the nasal inserts provided herein, wherein the leaf and thread-like or string-like/spring-like elements comprise a component that is delivered over time, in response to a trigger.

Any of the nasal inserts provided herein, further comprising a valve in communication with the passageway, wherein the valve permits air and/or other components in one direction in the passageway.

Any of the nasal inserts provided herein, wherein the valve is a flap that permits air and/or other components to proceed in one direction through the passageway.

Any of the nasal inserts provided herein, wherein the valve is defined in the body of the insert and permits air and/or other components to proceed in one direction through the body, Any of the nasal inserts provided herein, wherein the valve is in communication with the body and/or the passageway and permits air and/or other components to fully, partially, or selectively, proceed through the passageway.

Any of the nasal inserts provided herein, further comprising: a non-sealable deflector extending from the body to deflect the flow external to the passageway.

Also provided herein is a nasal insert for insertion in a nasal cavity comprising: a body; a hook attached to the body to hold the body in place; and a flat leaf comprising a component able to produce a required effect, wherein the flat leaf extends from the body, wherein the leaf is not a seal.

Any of the nasal inserts provided herein, wherein the leaf and body are made of a heat-sensitive/humidity sensitive, or other reactivity sensitive material that will dissipate over a period of time.

Any of the nasal inserts provided herein, wherein the body further comprises a thread-like element extending from the body, the thread-like element having a component able to create a required effect to a user.

Any of the nasal inserts provided herein, wherein the body further comprises a thread-like element extending from the body, wherein the thread-like element is made of a heat-sensitive/humidity sensitive or other reactivity sensitive material that will dissipate over a period of time.

Any of the nasal inserts provided herein, wherein the thread-like element comprises or is a unitary body.

Any of the nasal inserts provided herein, further comprising a deflector extending from the body to deflect flow across the body.

Any of the nasal inserts provided herein, wherein the body includes a passageway configured to direct flow over the leaf.

Also provided herein is a nasal insert for insertion into the nasal cavity comprising a body, the body having an inner surface and an outer surface, the inner surface configured to form a passageway with a surface of the nasal cavity and to permit flow of air and/or other components.

Also provided is a nasal insert comprising a body configured to be inserted into a nasal cavity, and a thread-like element extending from the body comprising a component able to create a required effect for a user.

Any of the nasal inserts provided herein, further comprising a seal attached to the thread-like element.

Further provided herein is a method for treating/assisting an ailment, or for other uses comprising the steps of: providing a nasal insert, said nasal insert comprising a body having an inner surface defining a passageway and an outer surface, wherein the body extends along a path to direct flow to a specific region of the nasal cavity or beyond it through the first passageway; inserting said nasal insert body into the nasal cavity; wherein the nasal insert body is configured to either (1) directs the air and/or any substance towards the olfactory region, and/or towards other regions of the nasal cavity or beyond and/or to manipulate the air/any substance in relation to these regions, and/or (2) wherein the nasal insert create a bypass of the olfactory region or other specific region in the nasal cavity or beyond it, or direct air/any substance away from the olfactory region or other defined region in the nasal cavity or beyond it, thereby delaying, blocking, or reducing the amount of or manipulating the any substance from reaching the olfactory, or being in close proximity to the olfactory region, and/or to other regions of the nasal cavity or beyond, and/or (3) wherein the nasal insert is configured to manipulating the olfactory, and/or other region in the nasal cavity or beyond; and wherein the redirection of the any substance, and/or the blocking or reducing or manipulation of the any substance and/or the olfactory region alters or diminishes bodily processes thereby producing a therapeutic or other effect.

The above method, wherein insertion of the nasal insert into the nasal cavity blocks, prevents, reduces, or delays smelling.

The above method, wherein the nasal insert contains or comprises a medicine and/or a hormone and/or analog and/or antagonist and/or oxygen and/or odor, and/or bacteria, and/or nano-particles.

The above method, wherein the nasal insert is configured to be positioned in any of the nasal meatuses or required area in the nasal cavity.

The above method, wherein the nasal insert is used in a duration and/or situation, and/or frequency according to the specific definition to produce the required therapeutic or wellness or other effect.

The above method, wherein the nasal insert is worn for providing a therapeutic substance, and wherein the nasal insert is positioned in a user such that the therapeutic substance reaches a target destination, thereby providing a therapeutic effect.

The above method, wherein the wearing of the nasal insert body creates a feeling of a mild cold and/or light runny nose, and/or a feeling of sickness or a feeling of disgust and/or less enjoyable or less comfortable experience resulting in the therapeutic effect.

The above method, wherein the wearing of the nasal insert body and manipulating the flow of air and other components creates a the therapeutic, wellness, or other required effect.

Also provided herein is a nasal insert for insertion in a nasal cavity comprising: a body and an expandable flat leaf, and wherein the body is a thread-like element.

Also provided is a nasal insert for insertion in a nasal cavity comprising: a body and thread-like elements extending therefrom, and wherein the nasal insert has an inner surface and an outer surface.

Any of the nasal inserts provided herein, wherein the thread-like elements extend extends from either the inner surface, the outer surface, or from both surfaces.

BRIEF DESCRIPTION OF THE DRAWINGS

In general all embodiments represent non-limiting examples of different variations to fulfill the same principles, of bringing a treatment to its destination within the nasal cavity or to target areas which are connected to it and leveraging nasal characteristics for it. For clarification, the following figures and their descriptions are provided as non-limiting examples.

FIG. 2 is a side elevated view of a nasal insert made in accordance with the present invention.

FIG. 3 is a top plan view of a nasal insert made in accordance with the present invention.

FIG. 4 is a front elevated view of another embodiment of the nasal inset made in accordance with the present invention.

FIG. 5 is a front elevated view of a nasal insert made in accordance with the present invention.

DETAILED DESCRIPTION

Figure 1:
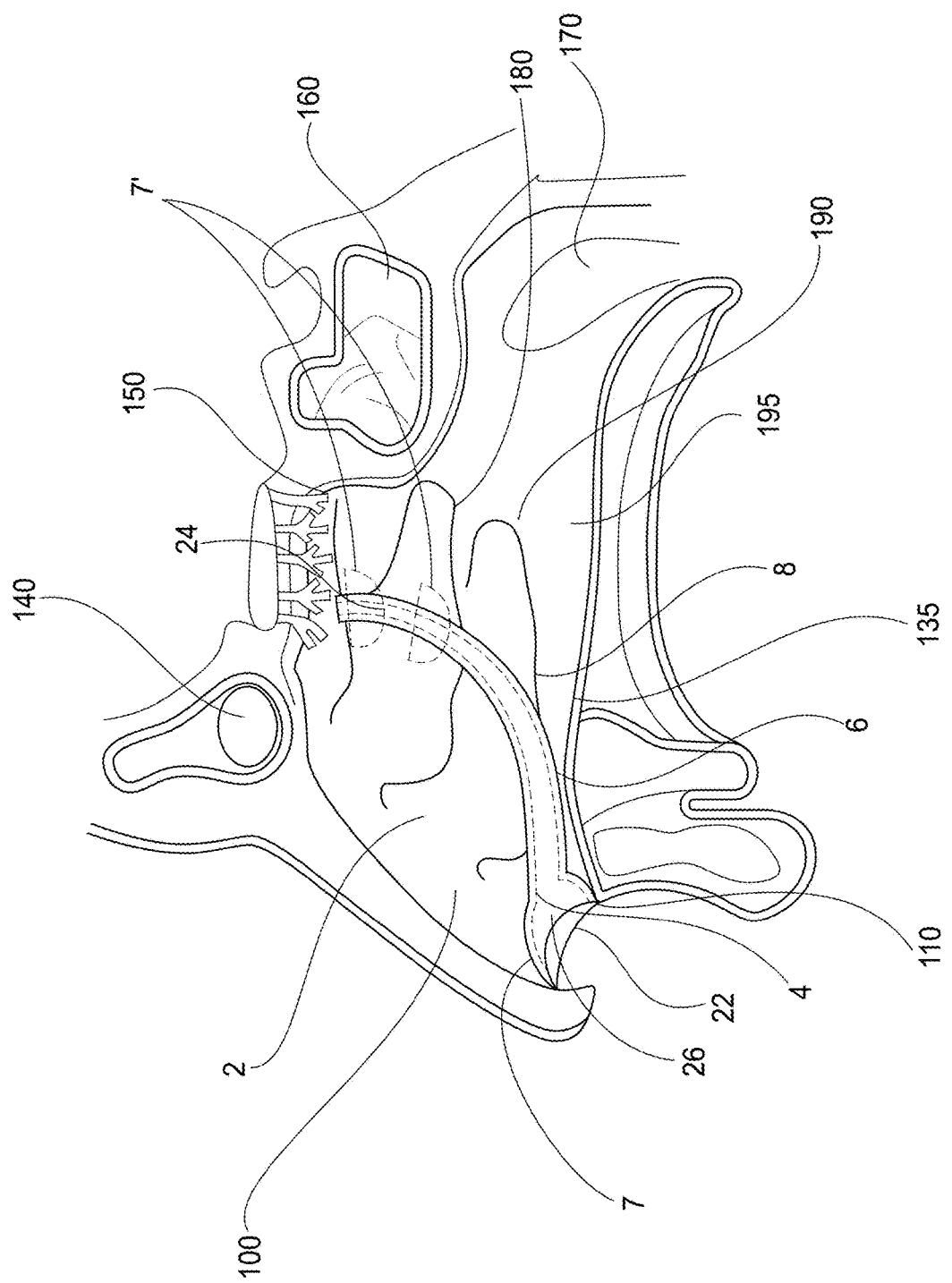
FIG. 1 is a side elevated view of a nasal insert made in accordance with the present invention contained within a nasal passageway.

It will be readily appreciated by those skilled in the art that modifications may be made to the invention without departing from the concepts disclosed in the foregoing description. Accordingly, the particular embodiments described in detail herein are illustrative only and are not limiting to the scope of the invention, which is to be given the full breadth of the appended claims and any and all equivalents thereof.

As described herein, the present insert can include a combination of none, one or more pipe passageways, none, one or more seals, none, one or more threads, none, one or more anchors, none, one or more membranes/valves etc., and none, one or more leafs or sheets, also it may or may not have a head. This present application shows different embodiments but the features of the embodiments may be combined with other embodiments. Further, the shapes of the various embodiments (for example, the seals, threads, leafs, anchors/hooks/holdfasts etc.) are not limited to the shapes depicted by the appending Figures. Rather, any suitable shape may be utilized in order to achieve the intended effect.

Provided herein are apparatuses for treatment via nasal cavity through efficient drug delivery, or other treatment, or through other manipulation done to or via the nasal cavity. The apparatuses detailed in the present invention may serve for any treatment that can be provided via the nasal cavity. By wearing the nasal insert, the air/molecules/odors/substances/signals/inputs from the outside environment or from inside the body can be manipulated and leveraged for achieving desired affects. The apparatuses may provide access of such particles/signals/materials/etc. to specific areas and/or prevent them from specific areas. The apparatuses detailed herein enable direct and efficient drug and/or other substance(s)/signal(s)/etc. delivery to any desirable area within the nasal cavity or through the nasal cavity, as well to prevent such elements from other areas as needed. The target organ to treat may be located inside the nasal cavity or may be accessed via the nasal cavity, for example: but not limited to the brain, olfactory region, the sinuses, nasal mucosa, lungs, throat, CNS, blood stream, etc.

The olfactory region concentrates a significant interest for treatment, and is, as explained, hard to reach. In the context of this invention, olfactory is related to not only as nose to brain delivery channel but in a broader aspect. It is known that olfactory cells exist not only in the nose but also in many internal organs, for example in the kidneys in the gut in the heart, and in the blood. These olfactory internal cells are assumed to be functioning as sensors managing "input/output" bodily decisions and other activities. Based on the above, and on other observations, it is my belief that olfactory cells in the nose may serve as the main bio-chemical interface and sensor of the brain and hypothalamus with the environment, including with foods' odors-environmental and in the mouth—that are reaching the nose, and including other environmental inputs. Also the nose olfactory receives many bodily internal inputs via many channels. For example: via throat mouth and digestive system, via the different nerves, via the blood system, the CNS, the respiratory system and maybe via some connectivity to other olfactory cells that is done via different channels. etc. since olfactory serves as a critical bio-chemical sensor of the brain and affecting many bodily processes, manipulating it is expected to have affect over brain and over many bodily cycles. For example, once smelling in the nose is inhibited it may shut down or interfere with the regular metabolic cycle and other cycles in a very acute manner, since it blocks the hypothalamus' sensors from the relayed environmental chemical related inputs metabolic and non-metabolic (food, sex-pheromones, alcohol and many others). In this aspect, the hypothalamus (and brain in general) may then remain with other internal food/metabolic hormonal/other related signals, coming from internal olfactory cells, coming to nose olfactory cells or reaching the brain through other channels to dominate the related functionality. Another example would be that once a specific input is provided to or other manipulation is conducted to olfactory—for example—providing specific molecules and preventing the reach of other specific inputs, then a more sophisticated and accurate manipulation to brain and other bodily mechanisms can be achieved. Meaning, that the ability to manipulate olfactory in general, may provide us with the ability to create a comprehensive change in many bodily mechanisms such as: cycle of hunger and satiation, cycle of sugar level management, sexual attraction and fertility related management, and others, this is in addition and much further beyond simple nose to brain delivery that is hard to achieve and is available via this invention as well. In other words, the role of the apparatuses of this invention is also to specifically serve as olfactory manipulating nasal devices in addition to their ability to deliver treatment to any nasal area or to organs that are connected to it as was explained in relation to target areas.

For purposes of the description hereinafter, the terms "upper", "lower", "right", "left", "vertical", "horizontal", "top", "bottom", "lateral", "longitudinal" and derivatives thereof, shall relate to the invention as it is oriented in the drawing figures. However, it is to be understood that the invention may assume various alternative variations, except where expressly specified to the contrary. It is also to be understood that the specific devices illustrated in the attached drawings, and described in the following specification, are simply exemplary embodiments of the invention. Hence, specific dimensions and other physical characteristics related to the embodiments disclosed herein are not to be considered as limiting.

In addition to the nasal inserts described herein, other exemplary nasal inserts and methods that may be used to achieve the methods described herein is described for example in U.S. Pat. Nos. 8,517,026 and 8,839,790, U.S. Design patent application Ser. No. 29/626,909, and U.S. patent application Ser. Nos. 14/480,908 and 16/014,354. Each of these patents/patent applications are incorporated herein by reference.

Figure 35:
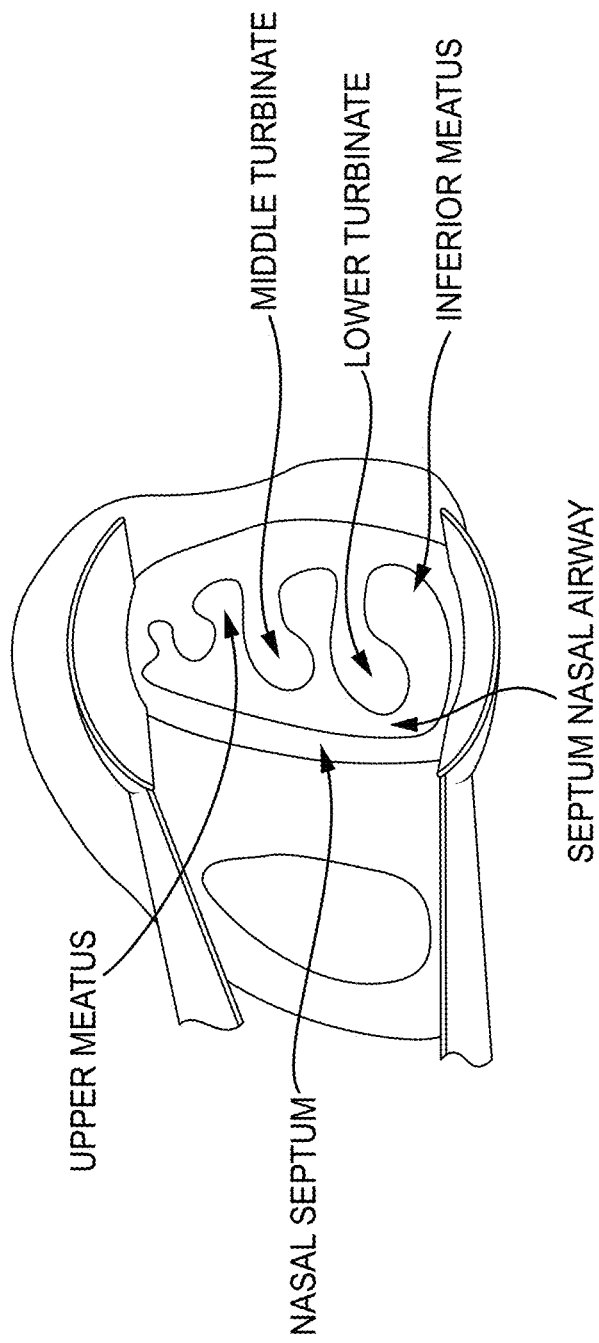
FIG. 35 is a picture of a nose. The left nostril is cross-section of the interior structure of the nasal cavity. Shown are the middle and lower turbinates, the upper and inferior meatuses, the nasal airway, and the nasal septum.
Figure 36:
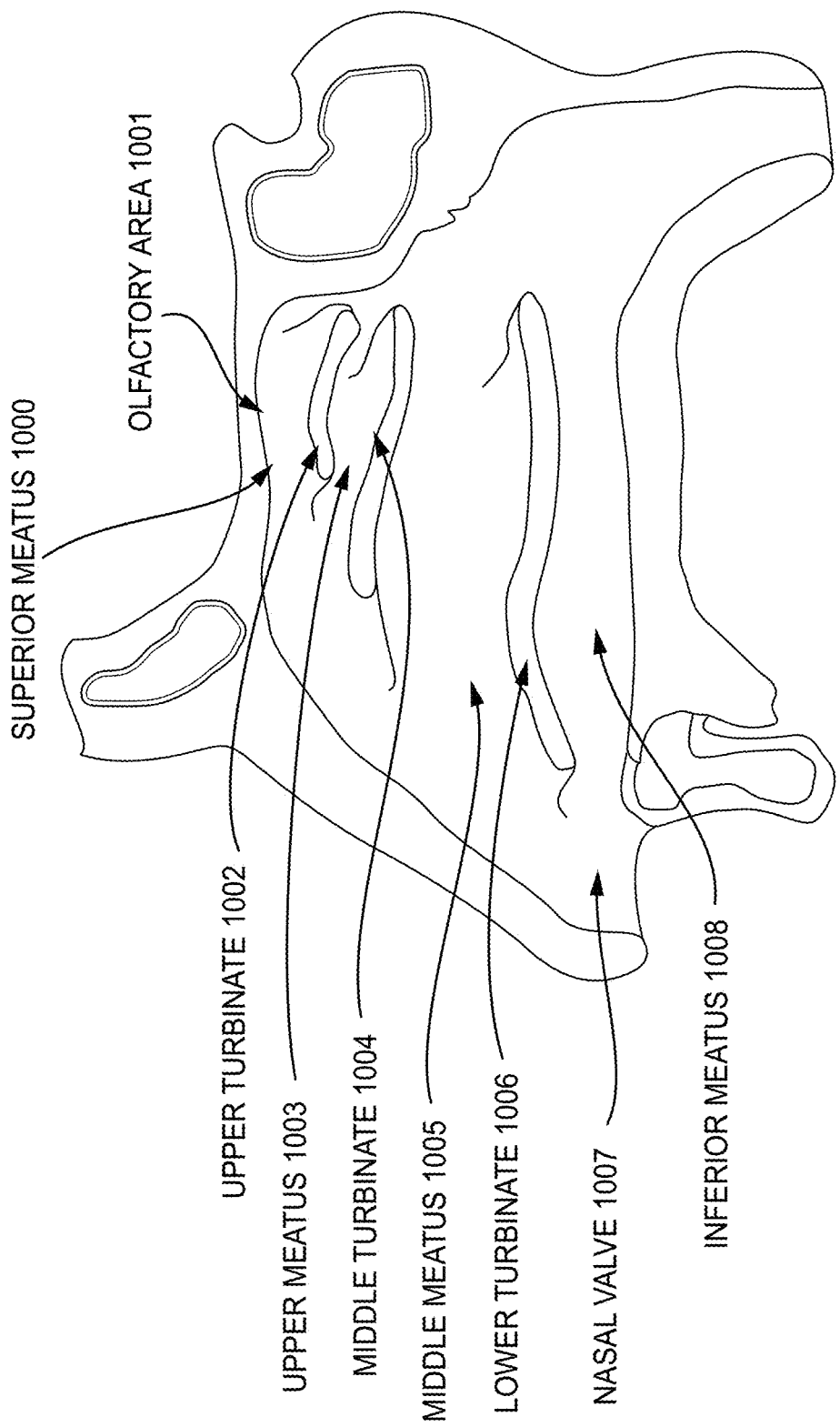
FIG. 36 is a side profile view of the left nostril of an individual showing the interior structure of the nasal cavity.

Nasal cavity 100, as shown in FIG. 1, includes a nostril 110, nasal floor 135 a frontal sinus 140, and an olfactory region 150. FIGS. 35 and 36 show the nasal cavity in more detail. FIG. 35 is a front cross section view of a left nasal passageway where the cross section line is beyond the nasal valve. FIG. 36 shows a profile cross section of a patent's nasal passageway FIGS. 35 and 36 show the environment of where the present nasal inserts are placed. The present invention can be used on either the left or right nasal passageways. The olfactory region 150 is covered by bipolar sensory neurons leaving the nose through the cribriform plate in the nasal roof synapsing in the olfactory bulb at the base of the frontal lobe of the brain. It is estimated that in the olfactory region 150, there are around six million sensory cells bilaterally. The olfactory senses reach the olfactory cortex in the rhinocephalon (not shown). Olfaction requires nasal air flow, which is part of respiration. The nasal cavities 100 further include nasal sinus 160 and nasopharynx 170. Also shown are the nasal conchas 180, 190. The inferior meatus 195 is located between the inferior concha 190 and the nasal floor 135.

With reference to FIGS. 1-34, embodiments of a nasal insert, generally indicated as 2, 2a, 2b, 2c, 2d, 2e, 2f, 2g, 2h, 2i, 2j, 2k, 2l, 2m, 2n, 2o, 2p, 2q, 2r, 2s, 2t, 2u, 2v, 2w, 2x, 2y, 2z, 2aa, 2bb, 2cc, 2dd, 2ee of the present invention are shown. The nasal inserts are used to deliver to a patient in need or to other user who wishes to have some beneficial wellness, therapeutic or other effect, thereof a material able to coact with the body or with the nasal insert body or a component able to create the required effect. By "wellness" it is meant to refer to non-medicament treatment that has an overall effect of advancing and/or improving the overall quality of life. For instance supplements, such as herbal supplements, such as *ginseng*. This includes medicament or non-medicament material, for instance, but not limited to, any sort of treatment, signals, molecules, nano-particles, bacteria, herbal and non-herbal material, environmental, by air, naturally exist or created in the body or outside of it, from in-body source, or other dedicatedly made, etc. The nasal inserts provided herein may also be used in order to prevent by preventing the material/component from reaching the olfactory or other areas.

Further, the nasal inserts of the present invention are able to direct both the incoming (inhaled) and outgoing (exhaled) flow of air and/or other components. By air and/or other components, it is meant herein to include air and any other components that might be included in that air, such as, but not limited to particles, smoke, pollutants, chemicals, bacteria, viruses, hormones, odors, electric or other signals, heat/temp, humidity, signals and materials etc. from in-body, from the environment, dedicatedly made or other, etc. The nasal inserts of the present invention are able to provide this functionality by having one or more passageways and other elements as described in this invention.

The figures are explained in detail below.

FIGS. 1 to 34 show various embodiments of the present invention that include passageways, threads, valves, leafs, seals etc. that are discussed in more detail below.

Provided herein are apparatuses for treatment via nasal cavity through efficient drug delivery, or other treatment, or through other manipulation done to or via the nasal cavity. The apparatuses detailed in the present invention may serve for any treatment that can be provided via the nasal cavity. By wearing the nasal insert, the air/molecules/odors/substances/signals/inputs from the outside environment or from inside the body or from other source as embedded into the device or connected to it can be manipulated and leveraged for achieving desired affects. The apparatuses may provide access of such particles/signals/materials/etc. to specific areas and/or prevent them from specific areas. The apparatuses detailed herein enable direct and efficient drug and/or other substance(s)/signal(s)/etc. delivery to any desirable area within the nasal cavity or through the nasal cavity, as well to prevent such elements from other areas as needed. The target organ to treat may be located inside the nasal cavity or may be accessed via the nasal cavity, for example: but not limited to the brain, olfactory region, the sinuses, nasal mucosa, lungs, throat, Central Nervous System (CNS), blood stream, etc.

The olfactory region concentrates a significant interest for treatment, and is, as explained, hard to reach. In the context of this invention, olfactory is related to not only as nose to brain delivery channel but in a broader aspect. It is known that olfactory cells exist not only in the nose but also in many internal organs, for example in the kidneys, in the gut, in the heart, and in the blood. These olfactory internal cells are assumed to be functioning as sensors managing "input/output" bodily decisions and other activities. Based on the above, and on other observations, it is believed that olfactory cells in the nose may serve as the main bio-chemical interface and sensor of the brain and hypothalamus with the environment, including with foods' odors-environmental and in the mouth—that are reaching the nose, and including other environmental inputs. Also the nose olfactory receives many bodily internal inputs via many channels. For example: via throat mouth and digestive system, via the different nerves, via the blood system, the CNS, the respiratory system and maybe via some connectivity to other olfactory cells that is done via different channels. etc. since olfactory serves as a critical bio-chemical sensor of the brain and affecting many bodily processes, manipulating it is expected to have affect over brain and over many bodily cycles. For example, once smelling in the nose is inhibited it may shut down or interfere with the regular metabolic cycle and other cycles in a very acute manner, since it blocks the hypothalamus' sensors from the relayed environmental chemical related inputs metabolic and non-metabolic (food, sex-pheromones, alcohol and many others). In this aspect, the hypothalamus (and brain in general) may then remain with other internal food/metabolic hormonal/other related signals, coming from internal olfactory cells, coming to nose olfactory cells or reaching the brain through other channels to dominate the related functionality. Another example would be that once a specific input is provided to or other manipulation is conducted to olfactory—for example—providing specific molecules and preventing the reach of other specific inputs, then a more sophisticated and accurate manipulation to brain and other bodily mechanisms can be achieved. Meaning, that the ability to manipulate olfactory in general, may provide us with the ability to create a comprehensive change in many bodily mechanisms such as: cycle of hunger and satiation, cycle of sugar level management, sexual attraction and fertility related management, and others, this is in addition and much further beyond simple nose to brain delivery that is hard to achieve and is available via this invention as well. In other words, the role of the apparatuses of this invention is also to specifically serve as olfactory manipulating nasal devices in addition to their ability to deliver treatment to any nasal area or to organs that are connected to it as was explained in relation to target areas.

FIG. 1 shows a nasal insert 2 inside of nasal cavity 100, as described above. Nasal insert 2 includes a body 8 that may be compressible. Body 8 may include an inner surface(s) 4 and an outer surface(s) 6. The inner surface(s) 4 of nasal insert body 8 defines an air passageway(s) 26. Nasal insert 2 additionally includes seals 7, proximate opening 22, and distal opening 24.

FIG. 2 shows a side view of a nasal insert 2a. Nasal insert 2a includes a body 8a that may be compressible. Body 8a may include an inner surface(s) 4a and an outer surface(s) 6a. The inner surface(s) 4a of nasal insert body 8a defines an air passageway(s) 26a. Nasal insert 2a, seals 7a, a proximate opening 22a, and a distal opening 24a.

FIG. 3 shows a nasal insert 2b. Nasal insert 2b includes a body 8b that may be compressible. Body 8b may include an inner surface(s) 4b and an outer surface(s) 6b. The inner surface(s) 4b of nasal insert body 8b defines an air passageway(s) 26b. Nasal insert 2b additionally includes seals 7b, a proximate opening 22b, and a remote/distal opening 24b. This insert may serve for example for insertion into the left nostril. It then enters deeper into the nasal cavity beyond the nasal valve, rests in one of the nasal cavity meatuses (inferior, middle, upper etc.), and it curves towards the nasal septum and then up and may provide treatment to olfactory.

FIG. 4 shows a nasal insert 2c. Nasal insert 2c includes a body 8c that may be compressible. Body 8c may include an inner surface(s) 4c and an outer surface(s) 6c. The inner surface(s) 4c of nasal insert body 8c defines an air passageway(s) 26c. Nasal insert 2c additionally includes a proximate end (which may or may not be bulbous in shape), seals 7c, a proximate opening 22c, and a distal opening 24c.

FIG. 5 shows a nasal insert 2d. Nasal insert 2d includes a body 8d that may be compressible. Body 8d may include an inner surface(s) 4d and an outer surface(s) 6d. The inner surface(s) 4d of nasal insert body 8d defines an air passageway(s) 26d. Nasal insert 2d additionally, seals 7d, proximate opening 22d, and a distal opening 24d.

FIGS. 2, 3 and 5 may serve as illustrated side, top and front views of same device. In this case that goes beyond the nasal valve and via one of the meatuses and then curves towards the septum airway and then curves up towards olfactory The positioning of the pipe/air passageway within the inferior meatus is not meant to be limiting as it can be position in different locations in the nasal cavity such as for example (not limited to): the middle meatus, the septum airway etc. for example, in case the device will progress first via the septum airway, then it will not need to curve towards the septum airway in order to reach olfactory. FIG. 4 illustrates a different path which goes beyond the nasal valve and into the septum air passageway, and curves up and then towards the lateral side of the nasal cavity into one of the meatuses to provide treatment thereto—for example (not limited) into the middle meatus towards the sinus opening.

Figure 6:
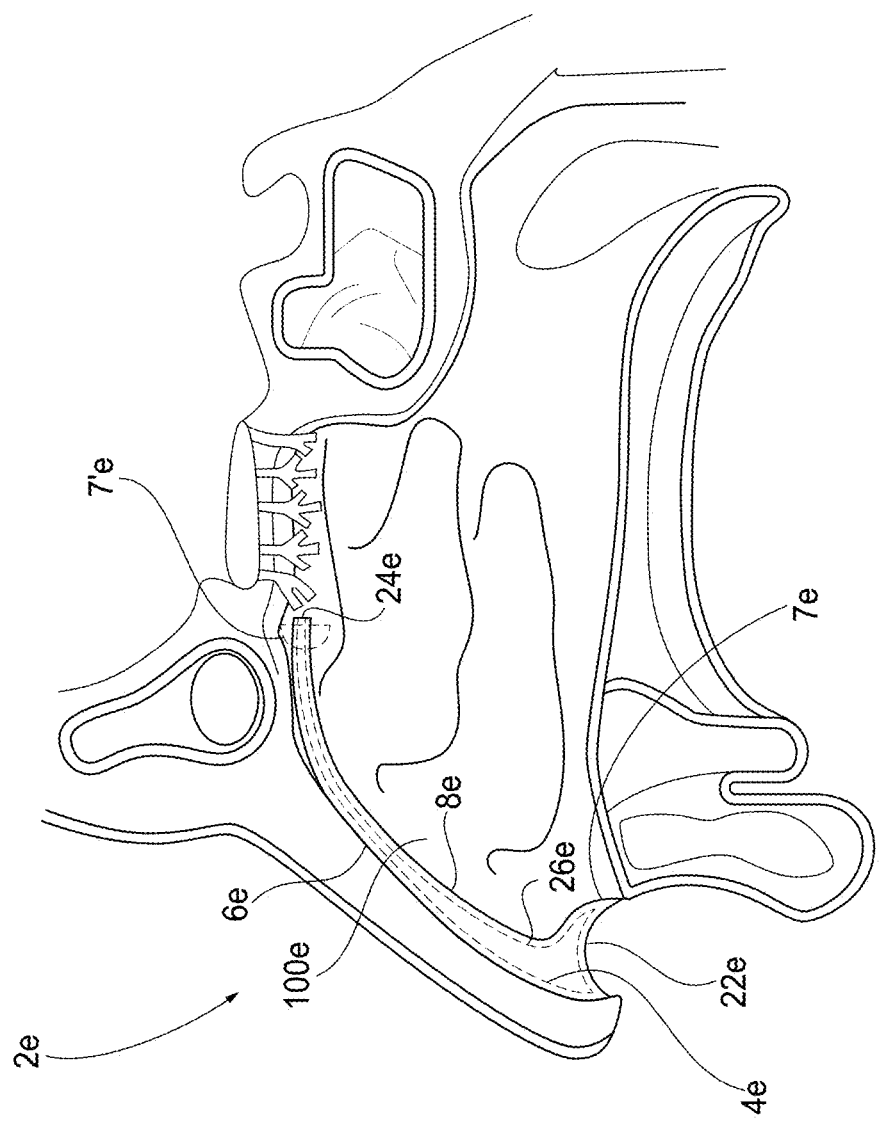
FIG. 6 is a side elevated view of an insert made in accordance with the present invention within the nasal cavity.

FIG. 6 shows a nasal insert 2e inside of nasal cavity 100e, as described above. Nasal insert 2e includes a body 8e that may be compressible. Body 8e may include an inner surface(s) 4e and an outer surface(s) 6e. The inner surface(s) 4e of nasal insert body 8e defines an air passageway(s) 26e, seals 7e, a proximate opening 22e, and a distal opening 24e.

Figure 7:
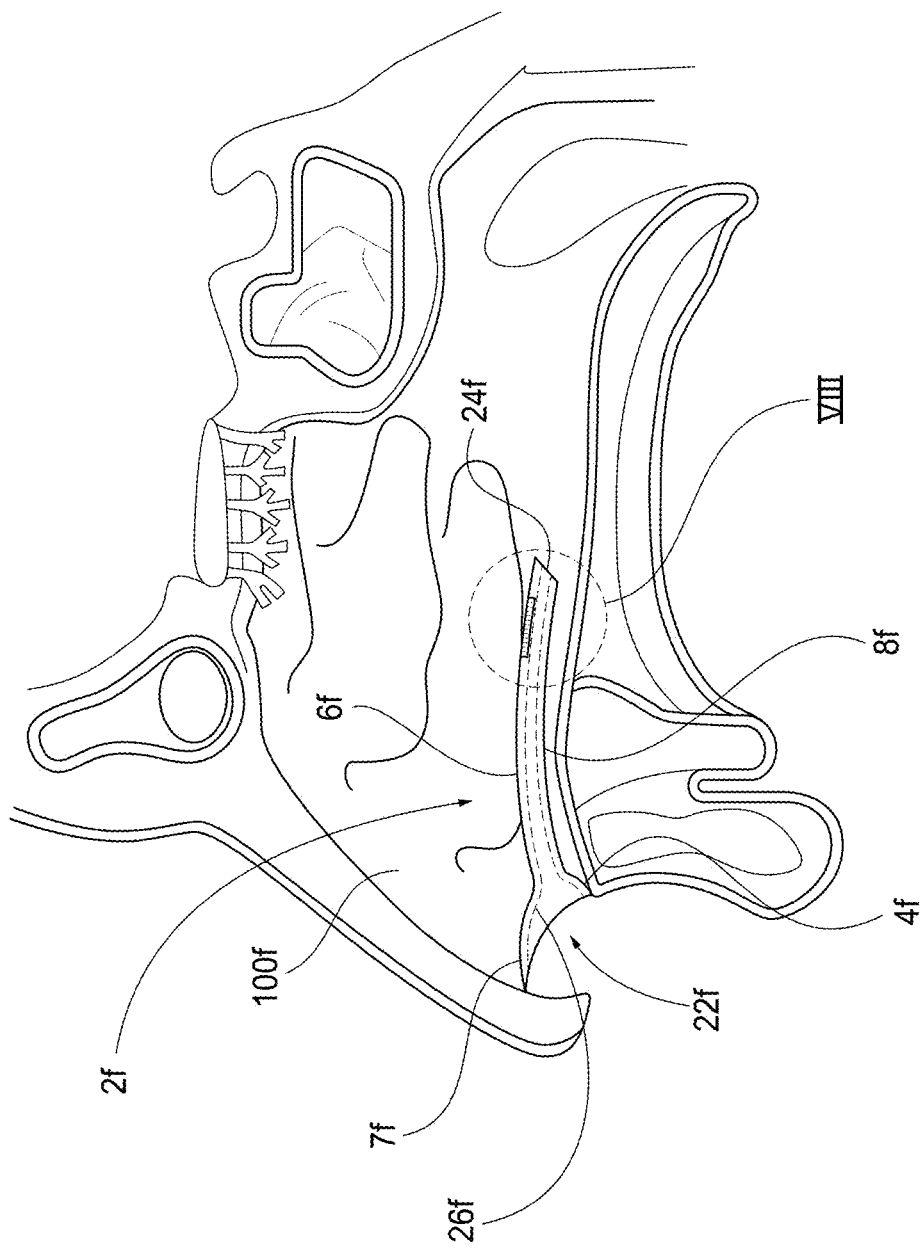
FIG. 7 is a side elevated view of an insert made in accordance with the present invention within the nasal cavity.

FIG. 7 shows a nasal insert 2f inside of nasal cavity 100f, as described above. Nasal insert 2f includes a body 8f that may be compressible. Body 8f may include an inner surface(s) 4f and an outer surface(s) 6f. The inner surface(s) 4f of nasal insert body 8f defines an air passageway(s) 26f. Nasal insert 2f includes a proximate end (which may or may not be bulbous in shape), seals 7f, a proximate opening 22f, and a distal opening 24f. Nasal insert 2f additionally includes the feature of FIG. 8 (marked VIII in FIG. 7), which is explained in detail below.

Figure 8:
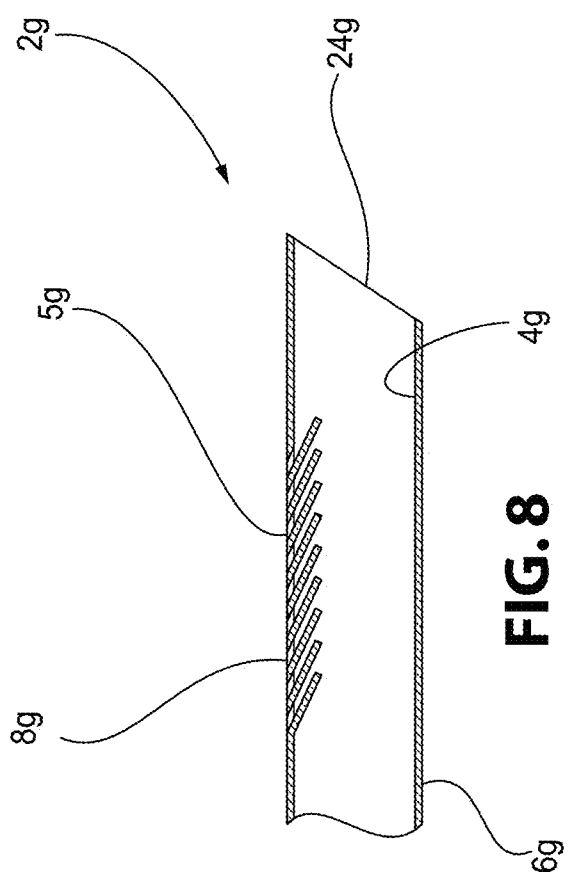
FIG. 8 is a partial sectional view of the insert shown in FIG. 7.

FIG. 8 shows an enlargement of VIII shown in FIG. 7. FIG. 8 shows a nasal insert 2g including a valve 5g (which may include also a membrane seal or be without one), an inner surface 4g, an outer surface 6g, and a distal opening 24g. Also shown in FIG. 8 is the direction of incoming air/other element flow. Air/other flow enters nasal insert 2g in the via opening 22, and can also have opposite air/other flow entering from 24g moving outwards. When a user inhales or enters air/other flow, air/other flow enters the nasal insert 22g, and inhalation keeps valve 5g closed. Specifically, valve 5g includes a plurality of flexible flaps that flex in a closed manner when inhaling and flex open when exhaling or having other flow in the outwards direction. Of course the flaps can be arranged so that the flaps flex open when inhaling and flex closed when exhaling. When a user exhales, air exits the nasal insert, and exhalation opens valve 5g. This mechanism allows desired particles (such as medicaments that are provided on the nasal insert, or molecules coming from mouth, throat, lungs etc.) to reach desired receptors and locations within the nasal cavity but can help preventing external particles from entering that area. Additional passageway(s) and seals can be added to better directing the required elements and delivering them closer to a specific target area (see FIG. 10).

Figure 9:
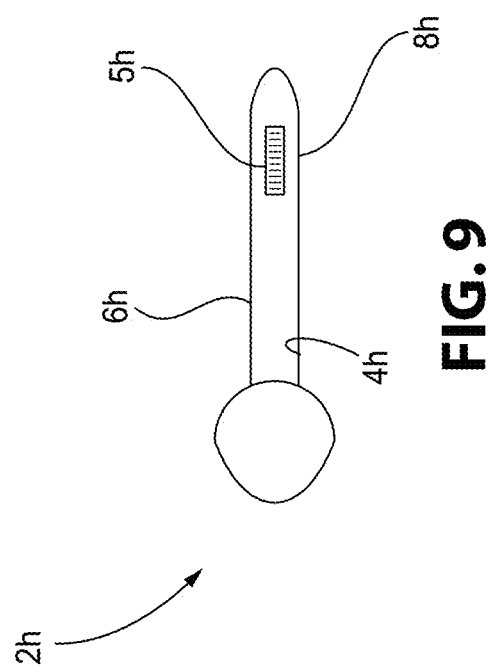
FIG. 9 is a top plan view of insert similar to the insert shown in FIG. 7.

FIG. 9 shows a top-down view of nasal insert 2h. Nasal insert 2h includes a body 8h that may be compressible. Body 8h may include an inner surface(s) 4h and an outer surface(s) 6h. Nasal insert 2h may additionally include a valve 5h, membrane(s), seal(s) etc. (not shown).

Figure 10:
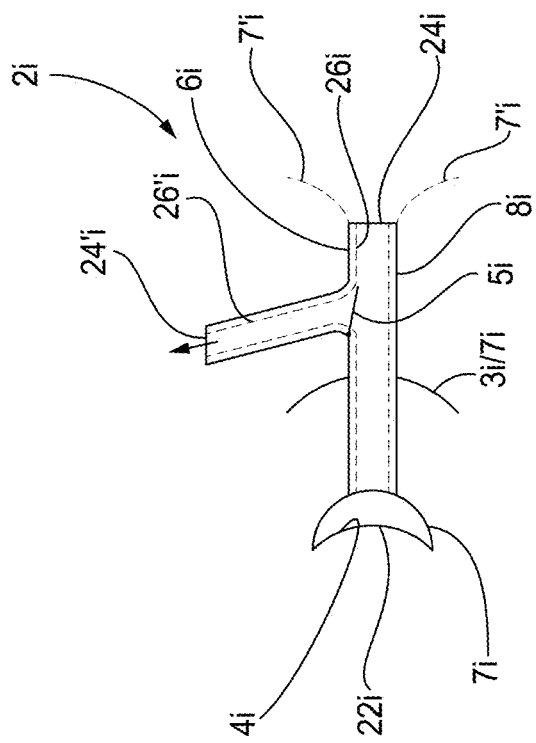
FIG. 10 is a side elevated view of another embodiment of a nasal insert made in accordance with the present invention.

FIG. 10 shows a side view of nasal insert 2i. Nasal insert 2i includes a body 8i that may be compressible. Body 8i may include an inner surface(s) 4i and an outer surface(s) 6i. The inner surface(s) 4i of nasal insert body 8i defines an air passageway(s) 26i, seals 7i or hooks 3i, a proximate opening 22i, and a distal opening 24i. Nasal insert 2i additionally includes a second passageway 26'i (with a second distal opening 24'i), a valve 5i (such as a flapper valve or other), and may also include additional seals 7'i (shown in phantom) at the tail of passageway 26i.

Figure 11:
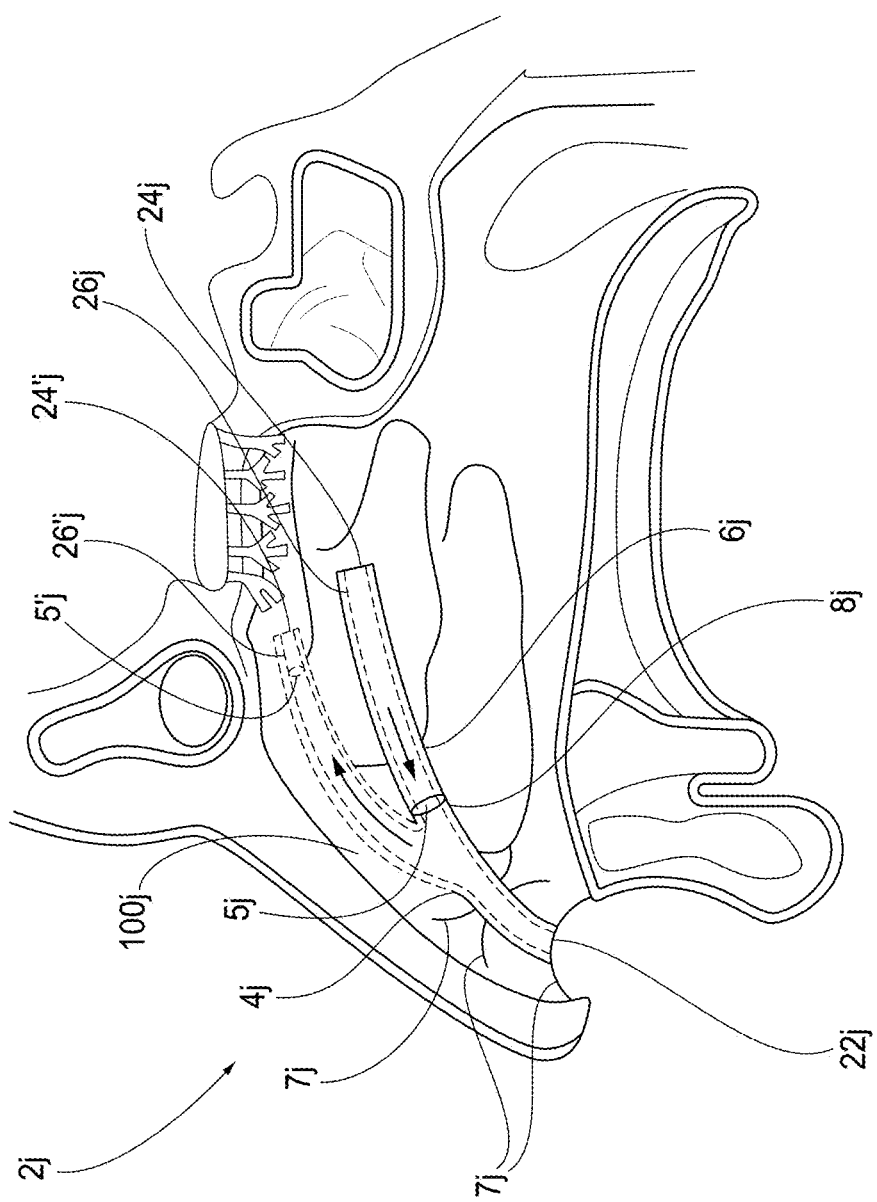
FIG. 11 is a side elevated view of a nasal insert made in accordance with the present invention within the nasal cavity.

FIG. 11 shows a nasal insert 2j inside of nasal cavity 100j, as described above. Nasal insert 2j includes a body 8j that may be compressible. Body 8j may include an inner surface(s) 4j and an outer surface(s) 6j. The inner surface(s) 4j of nasal insert body 8j defines an air passageway(s) 26j. Nasal insert 2j additionally includes seals 7j, valve 5j, proximate opening 22j, and a remote opening 24j. Note that 5j may be an optional valve and does not necessarily need to be present. Nasal insert 2j may also include a second passageway 26'j (shown in phantom) with a distal opening 24'j and an additional, optional valve 5'j. Valve(s) 5j/5'j may be flapper valve(s) or other valve and may or may not include a membrane. Valves 5j/5'j may for example either open or close depending whether the patient inhales or exhales. In one example, valve 5*j* may for example enable the pass of only outgoing flow, while valve 5'*j* may for example enable the flow of incoming flow. Passageway 26'*j* may then, for example, contain a treatment to be delivered for example to olfactory—leveraging incoming airflow for the delivery. All outgoing air flow will be directed to move through passageway 26*j* and will be avoided from passageway 26'*j*. In addition, in this or other embodiments, a valve may include also a membrane for enabling selective pass of components through it. This is one non-limiting example.

Figure 12:
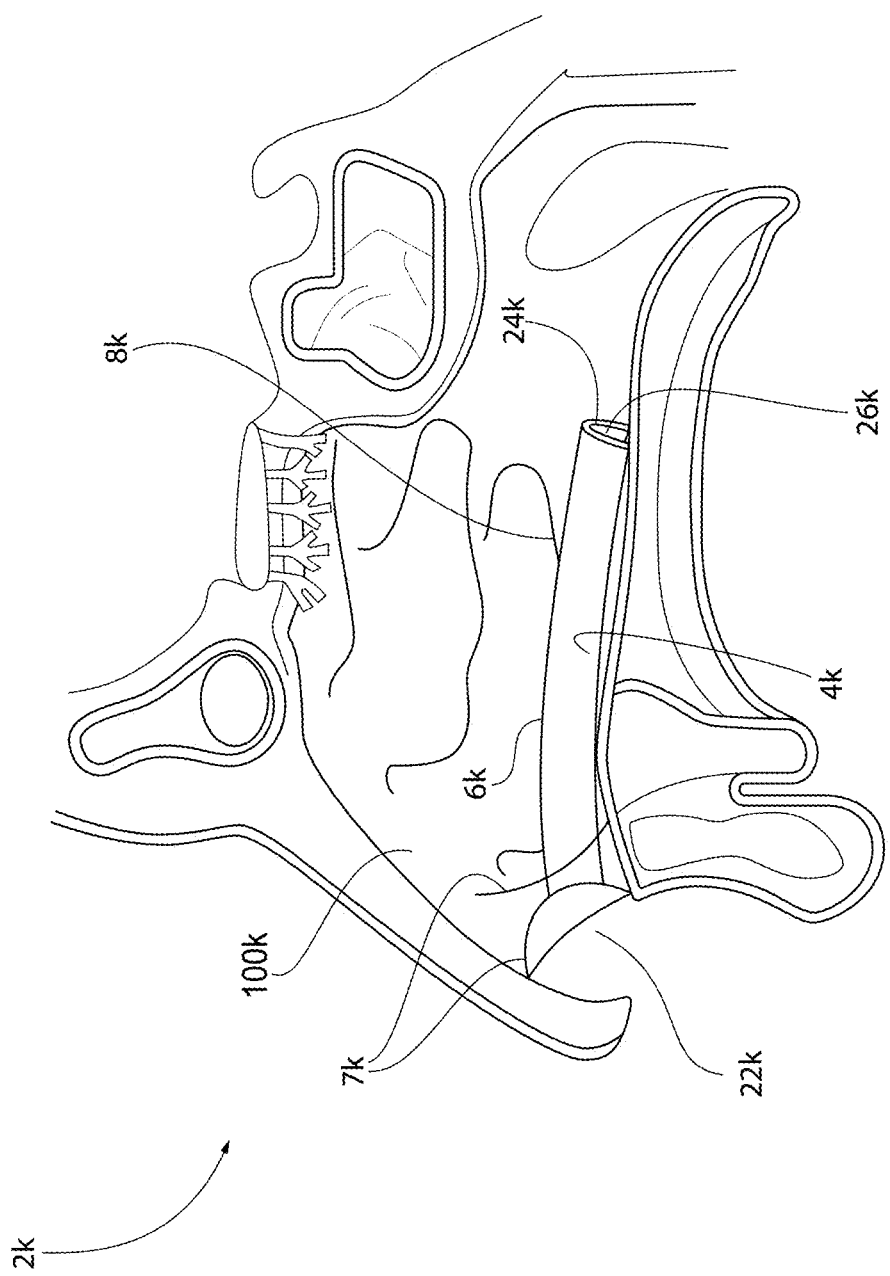
FIG. 12 is a side elevated view of a nasal insert made in accordance with the present invention within the nasal cavity.
Figure 14:
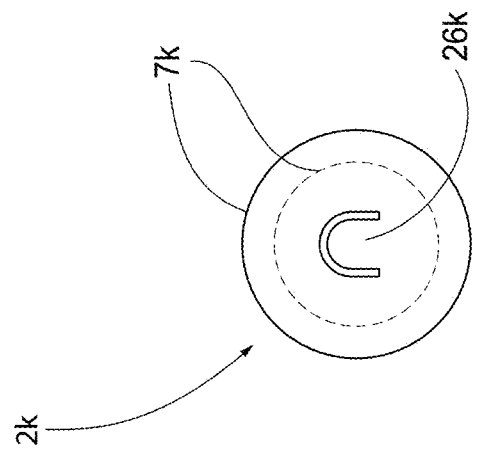
FIG. 14 is a rear plan view of the insert shown in FIG. 12.
Figure 13:
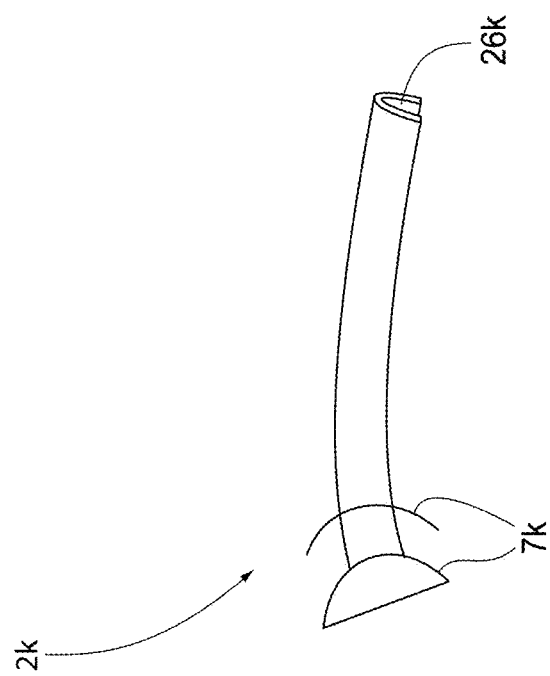
FIG. 13 is a side elevated view of a nasal insert similar to the insert of FIG. 12.

FIG. 12-14 shows a nasal insert 2*k* inside of nasal cavity 100*k*, as described above. Nasal insert 2*k* includes a body 8*k* that may be compressible. Body 8*k* may include an inner surface(s) 4*k* and an outer surface(s) 6*k* wherein the inner surface(s) 4*k* of nasal insert body 8*k* and the floor of the nasal cavity define an air passageway(s) 26*k*. Nasal insert 2*k* additionally includes, seals 7*k*, an upstream opening 22*k*, and a distal opening 24*k*. the formation of a passageway by a combination of the nasal insert body and the part of the nasal cavity is demonstrated here and is not limited to this configuration.

Figure 15:
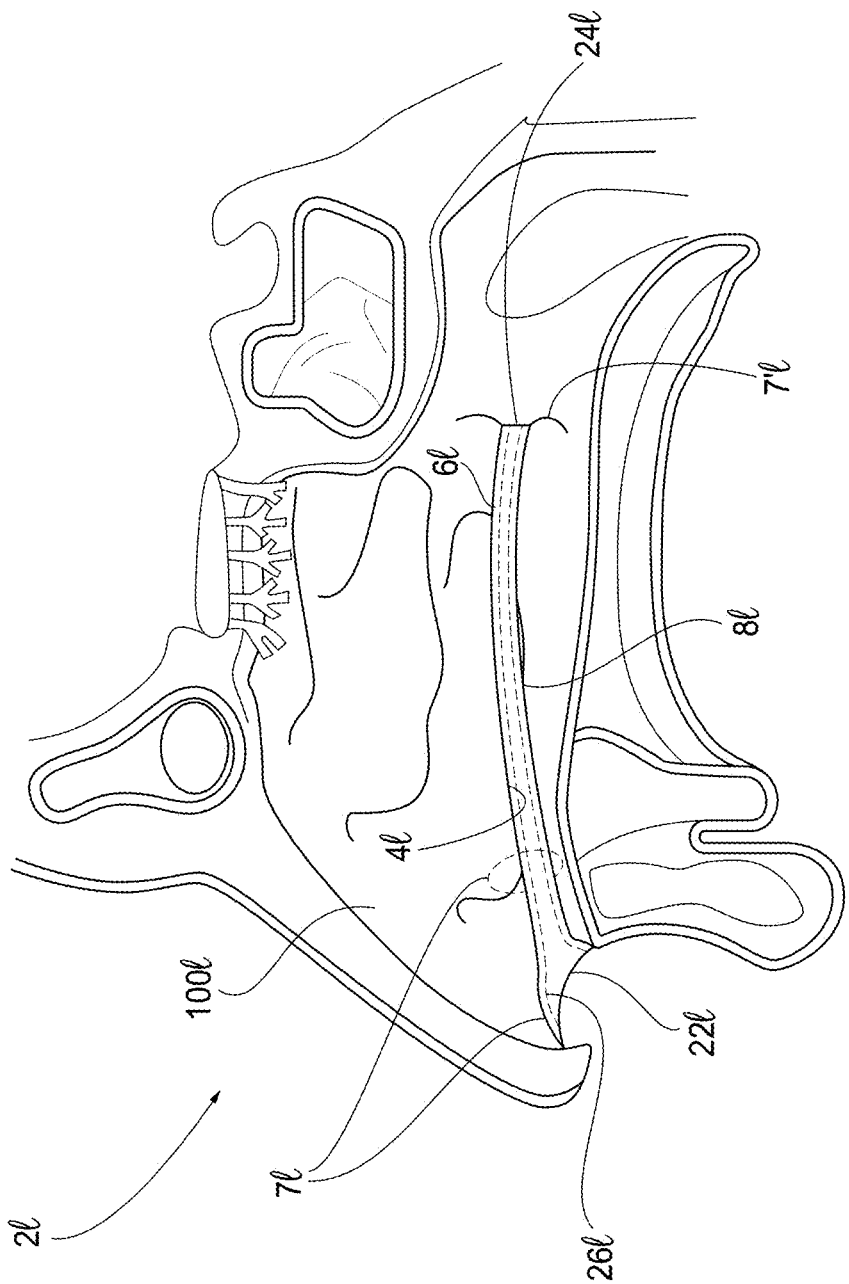
FIG. 15 is a side elevated view of an insert placed within a nasal cavity made in accordance with the present invention.

FIG. 15 shows a nasal insert 2*l* inside of nasal cavity 100*l*, as described above. Nasal insert 2*l* includes a body 8*l* that may be compressible. Body 8*l* may include an inner surface(s) 4*l* and an outer surface(s) 6*l*. The inner surface(s) 4*l* of nasal insert body 8*l* defines an air passageway(s) 26*l*. Nasal insert 2*l* additionally includes seals 7*l* (one of which is shown in phantom) and 7'*l* (wherein seals 7'*l* (as any other seal) may function as deflectors, blocking members, or shunts), an proximate opening 22*l*, and a distal opening 24*l*.

Figure 16:
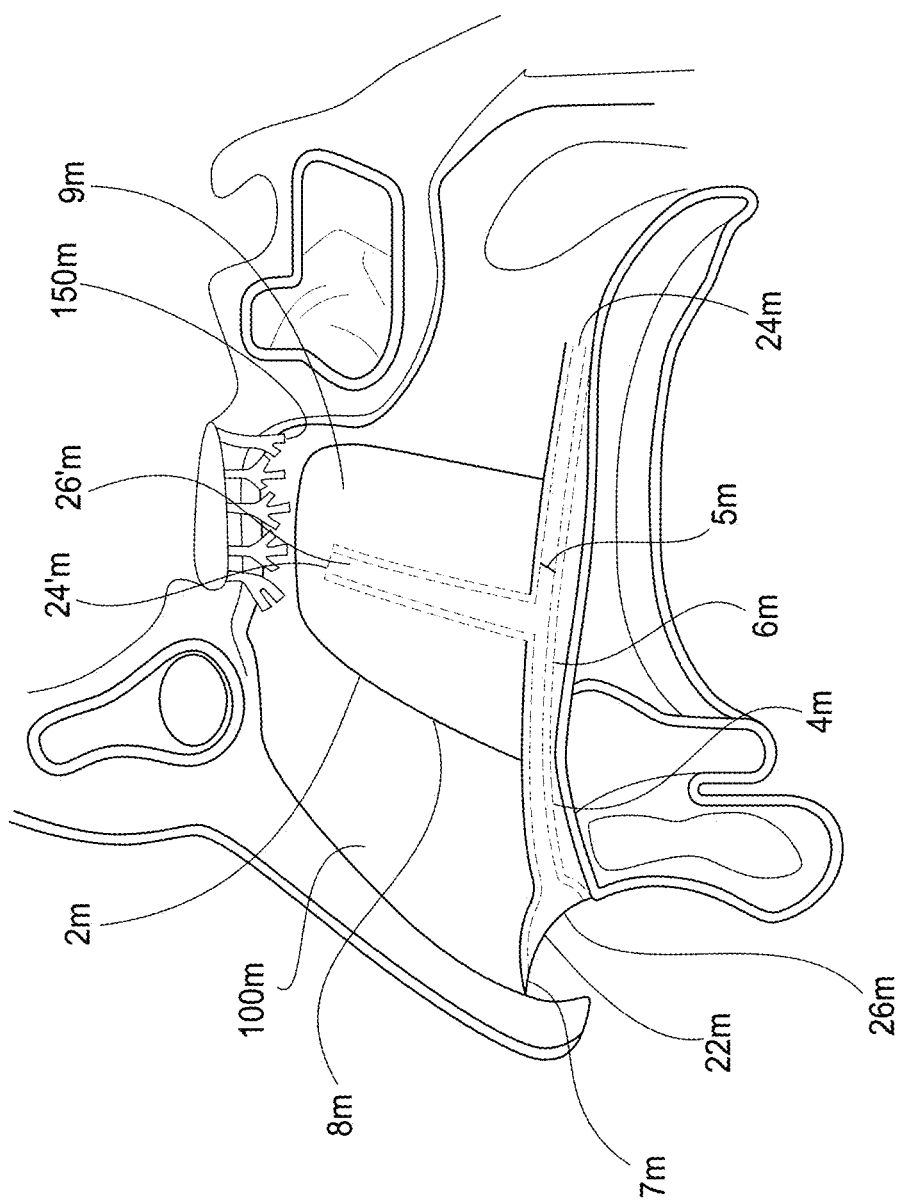
FIG. 16 is a side elevated view of an insert placed in a nasal cavity made in accordance with the present invention.

FIG. 16 shows a nasal insert 2*m* inside of nasal cavity 100*m*, as described above. Nasal insert 2*m* includes a body 8*m* that may be compressible. Body 8*m* may include an inner surface(s) 4*m* and an outer surface(s) 6*m*. The inner surface(s) 4*m* of nasal insert body 8*m* defines an air passageway(s) 26*m*. Nasal insert 2*m* includes, seals 7*m*, a proximate opening 22*m*, and a distal opening 24*m*. Nasal insert 2*m* may additionally include leaf-like structure or membrane 9*m*, wherein 9*m* may lean on the septum. 9*m* is inserted in a closed position but once inside the nasal cavity opens up into the leaf-like structure due to pressure, a spring like mechanism or in any other suitable manner. Leaf-like structure 9*m* may also additionally contain an additional passageway 26'*m* (shown in phantom), thereby defining an additional distal opening(s) 24'*m*, in order to direct air or aid in the delivery of medicine/treatment to specific regions of the nasal cavity (such as the olfactory region, defined in FIG. 16 as 150*m*). Leaf-like structure 9*m* may also contain more than one passageway.

Figure 17:
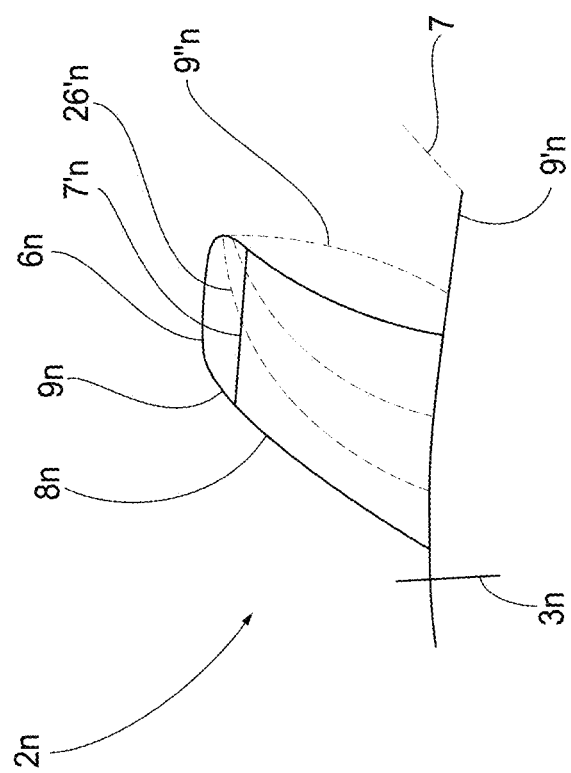
FIG. 17 is a side elevated view of an insert made in accordance with the present invention.

FIG. 17 shows a nasal insert 2*n* including a body 8*n* that may be compressible. Body 8*n* may include a surface(s) 6*n*, leaf-like structure 9*n*, and thread-like structures 9'*n* and/or 9"*n* (shown in phantom). The thread-like structures in FIG. 17 or in any embodiment of the present application may extend from any surface of the nasal insert body. For instance, it may extend from the inner surface, outer surface, or any surface therebetween. 9*n* is inserted in a closed position but once inside the nasal cavity opens up into the leaf-like structure due to pressure. Leaf-like structure 9*n* may also additionally contain an additional passageway 26'*n* (shown in phantom). Nasal insert 2*n* also includes hook 3*n*; which can engage with a wall of the nasal passageway.

Figure 18:
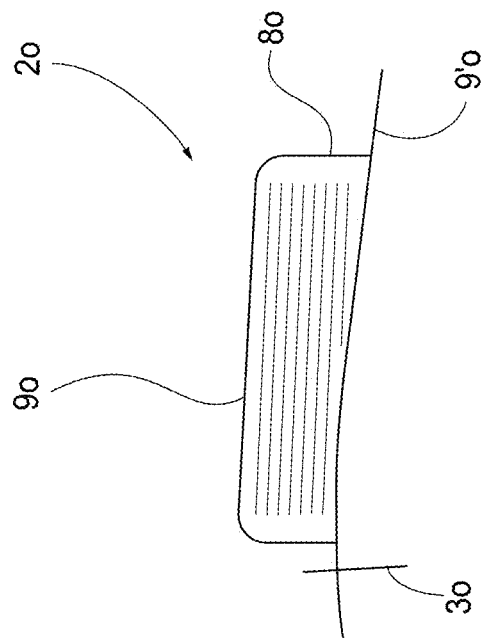
FIG. 18 is an example of a side closed view of the insert of FIG. 17 made in accordance with the present invention.

FIG. 18 shows a nasal insert 2*o* including a body 8*o* that may be compressible. Body 8*o* may include a surface(s) 6*o*, leaf-like structure 9*o*, and thread-like structure 9'*o*. 9*o* is inserted in a closed position but once inside the nasal cavity opens up into the leaf-like structure due to pressure or by other mechanism. Nasal insert 2*o* also includes hook 3*o* to engage with the walls of the nasal cavity.

Figure 19:
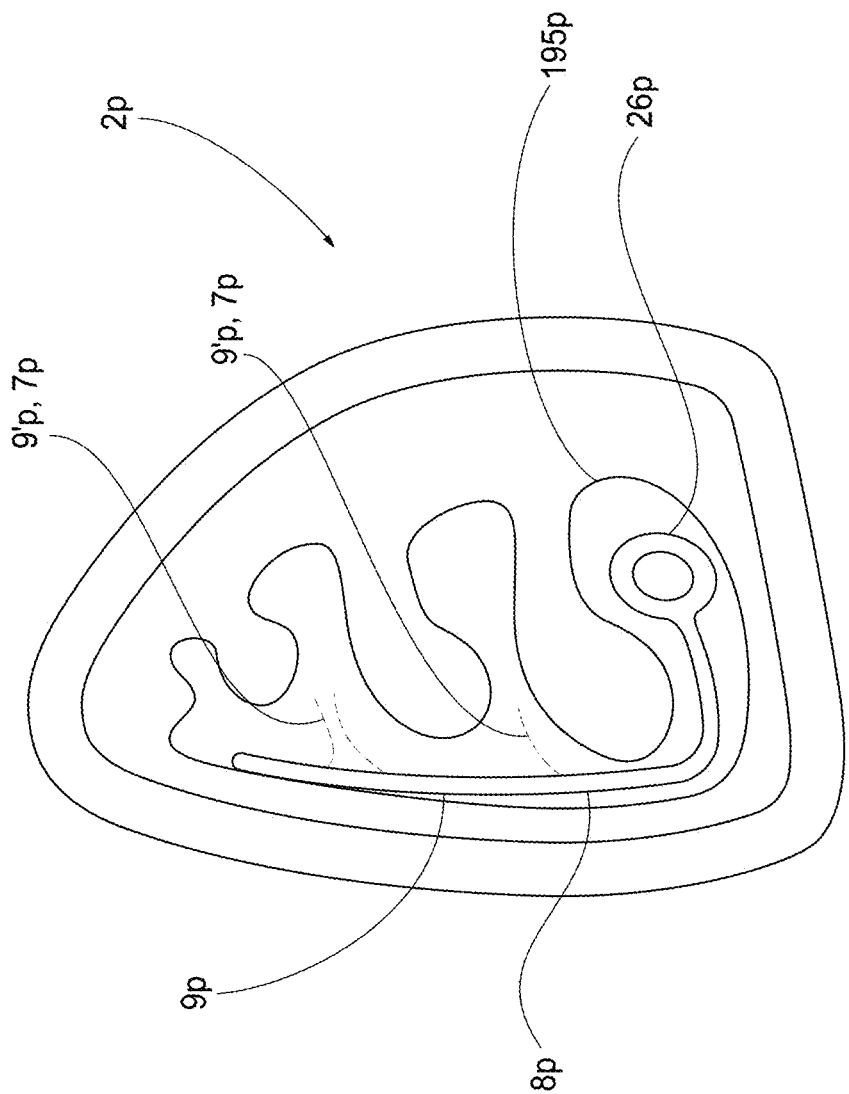
FIG. 19 is a front elevated view of an insert centered within the nasal passageway (cross section view) made in accordance with the present invention.

FIG. 19 shows a front cross section view of a nasal insert 2*p* including a body 8*p* that may be compressible. Note that the embodiment shown in FIG. 19 is a possible front, cross-sectional view of embodiment of FIG. 16. Body 8*p* of FIG. 19 may include a leaf-like structure 9*p* (which can be supported against the septum and conchas/meatuses, between the nasal cavity roof and nasal cavity floor), and thread-like structures 9'*p* and/or seals 7*p* (shown in phantom). Nasal insert 2*p* may also include a pipe defining a passageway 26*p*, wherein the pipe defining the passageway 26*p* is situated in this embodiment within the inferior meatus 195*p*. The pipe defining the passageway 26*p* directs air away from the leaf-like structure 9*p*. in another embodiment the air passageway 26*p* may direct part or all the air towards other leaf-like structure 9*p* or to other locations.

Figure 20:
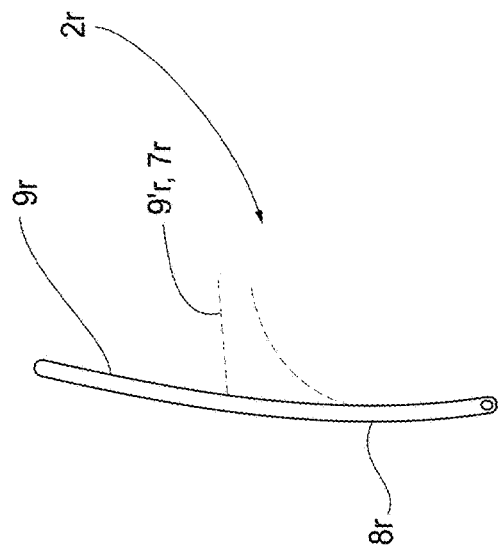
FIG. 20 is a front elevated view of a nasal insert made in accordance with the present invention.

FIG. 20 shows a nasal insert 2*q* including a body 8*q* that may be compressible. Body 8*q* may include a leaf-like structure 9*q* and thread-like structures 9'*q* and/or seals 7*q* (shown in phantom). Nasal insert 2*q* may also include a pipe defining a passageway 26*q*, and additional seal 7'*q* marked in phantom.

Figure 21:
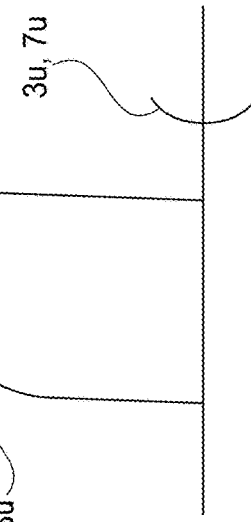
FIG. 21 is a front elevated view of a nasal insert made in accordance with the present invention.

FIG. 21 shows a nasal insert 2*r* including a body 8*r* that may be compressible. Body 8*r* may include a leaf-like structure 9*r* and thread-like structures 9'*r* or seals 7*r*.

Figure 22:
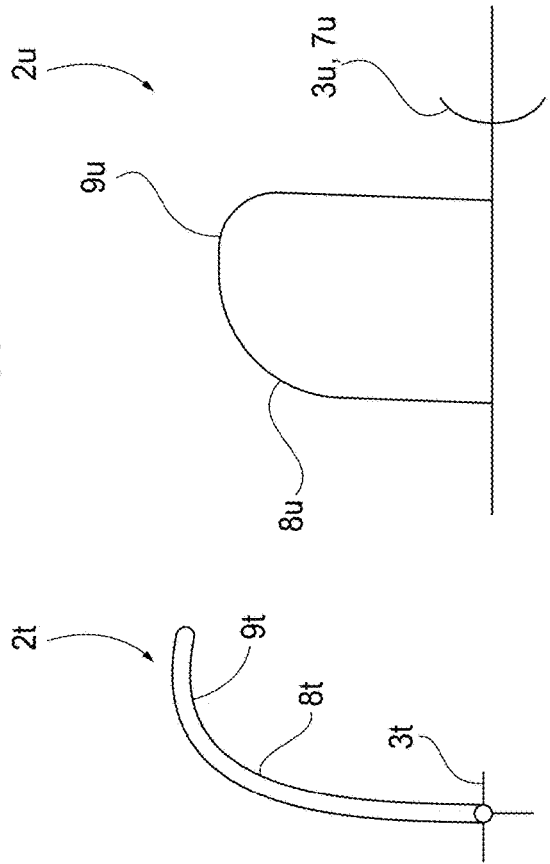
FIG. 22 is a front elevated view of a nasal insert made in accordance with the present invention.

FIG. 22 shows a nasal insert 2*s* including a body 8*s* that may be compressible. Body 8*s* may include a leaf-like structure 9*s* (and thread-like structures 9'*s* or seals 7*s* (shown in phantom). Nasal insert 2*s* may also include a pipe defining a passageway 26*s*.

Figure 23:
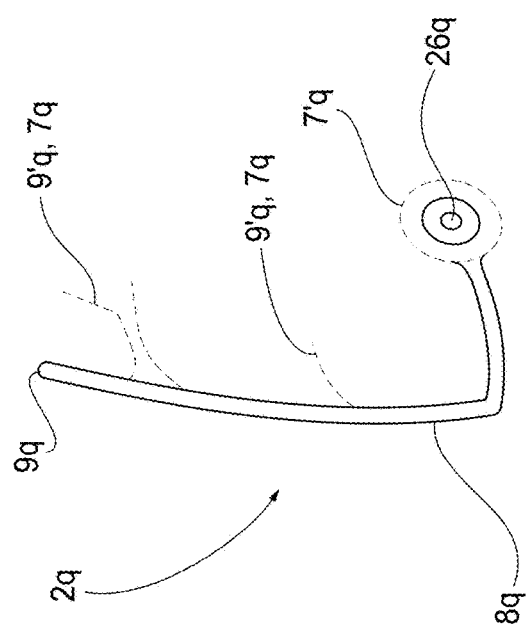
FIG. 23 is a front elevated view of a nasal insert made in accordance with the present invention.

FIG. 23 shows a front view of a 2*t* including a body 8*t* that may be compressible. Body 8*t* may include a leaf-like structure 9*t* and hook structures 3*t* to help keep the insert in place by engaging with the nasal.

Figure 24:
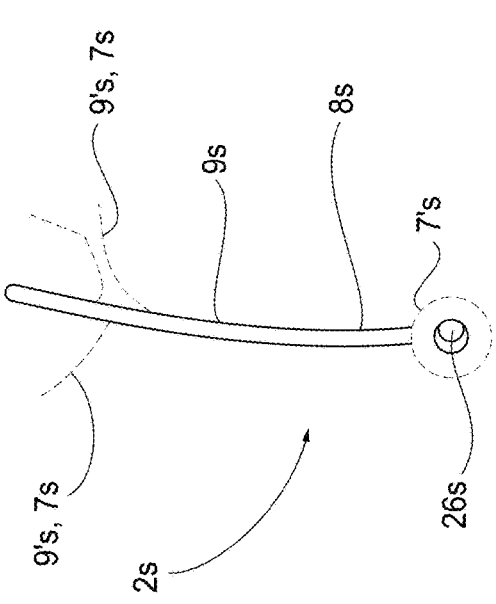
FIG. 24 is a side elevated view of a nasal insert made in accordance with the present invention.

FIG. 24 shows a side view of a 2*u* including a body 8*u* that may be compressible. Body 8*u* may include a leaf-like structure 9*u* (shown in an open-formation) and hook structures 3*u* to help keep the insert in place by engaging with the nasal cavity.

Figure 25:
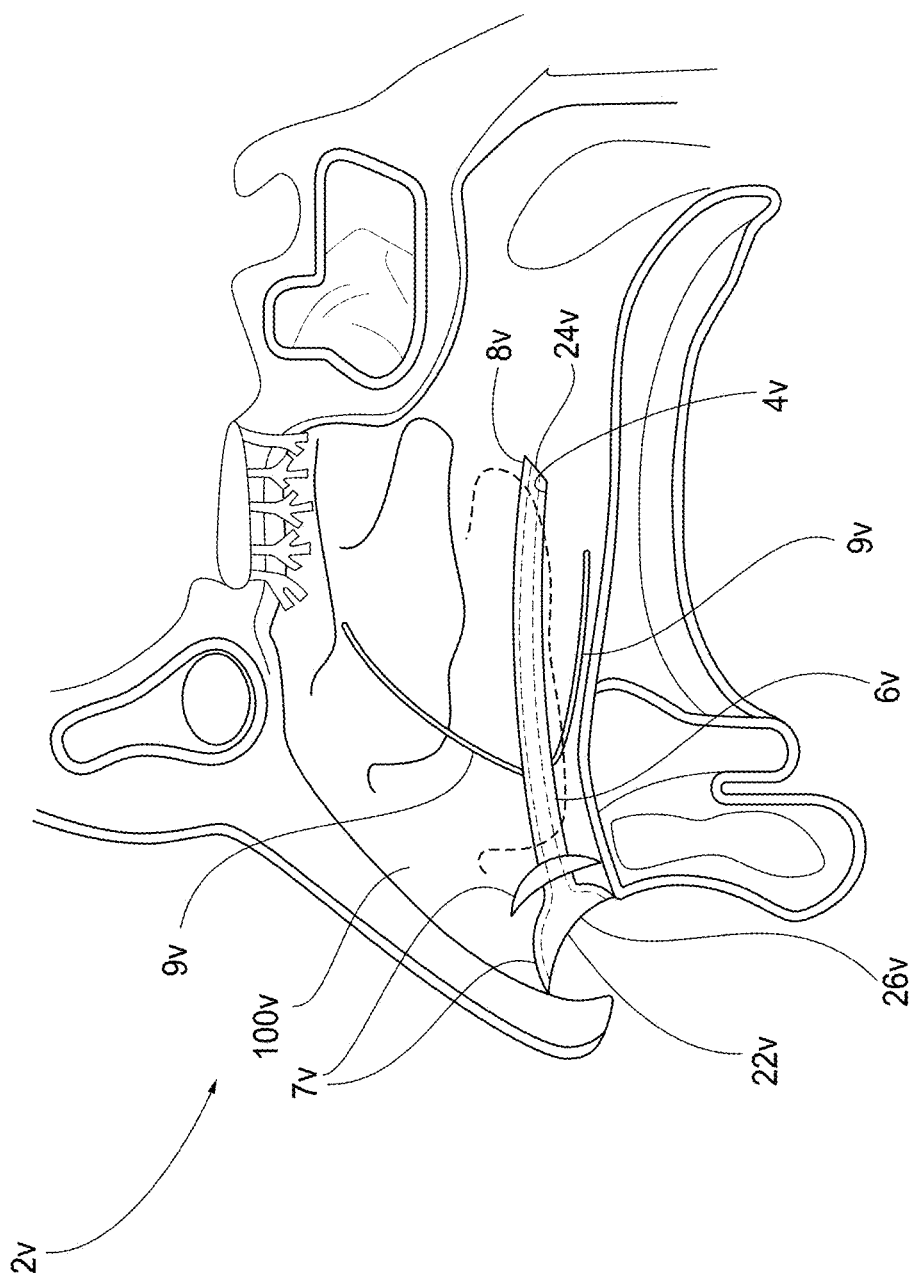
FIG. 25 is a side elevated view of a nasal insert contained within a nasal cavity made in accordance with the present invention.

FIG. 25 shows a nasal insert 2*v* inside of nasal cavity 100*v*. Nasal insert 2*v* includes a body 8*v* that may be compressible. Body 8*v* may include an inner surface(s) 4*v* and an outer surface(s) 6*v*. The inner surface(s) 4*v* of nasal insert body 8*v* defines an air passageway(s) 26*v*. Nasal insert 2*v* includes seals 7*v*, a proximate opening 22*v*, and a distal opening 24*v*. Nasal insert 2*v* may additionally include a thread-like structure 9*v*. Additional thread-like structures 9'*v* and seals 7'*v* may also be included (not shown).

Figure 26:
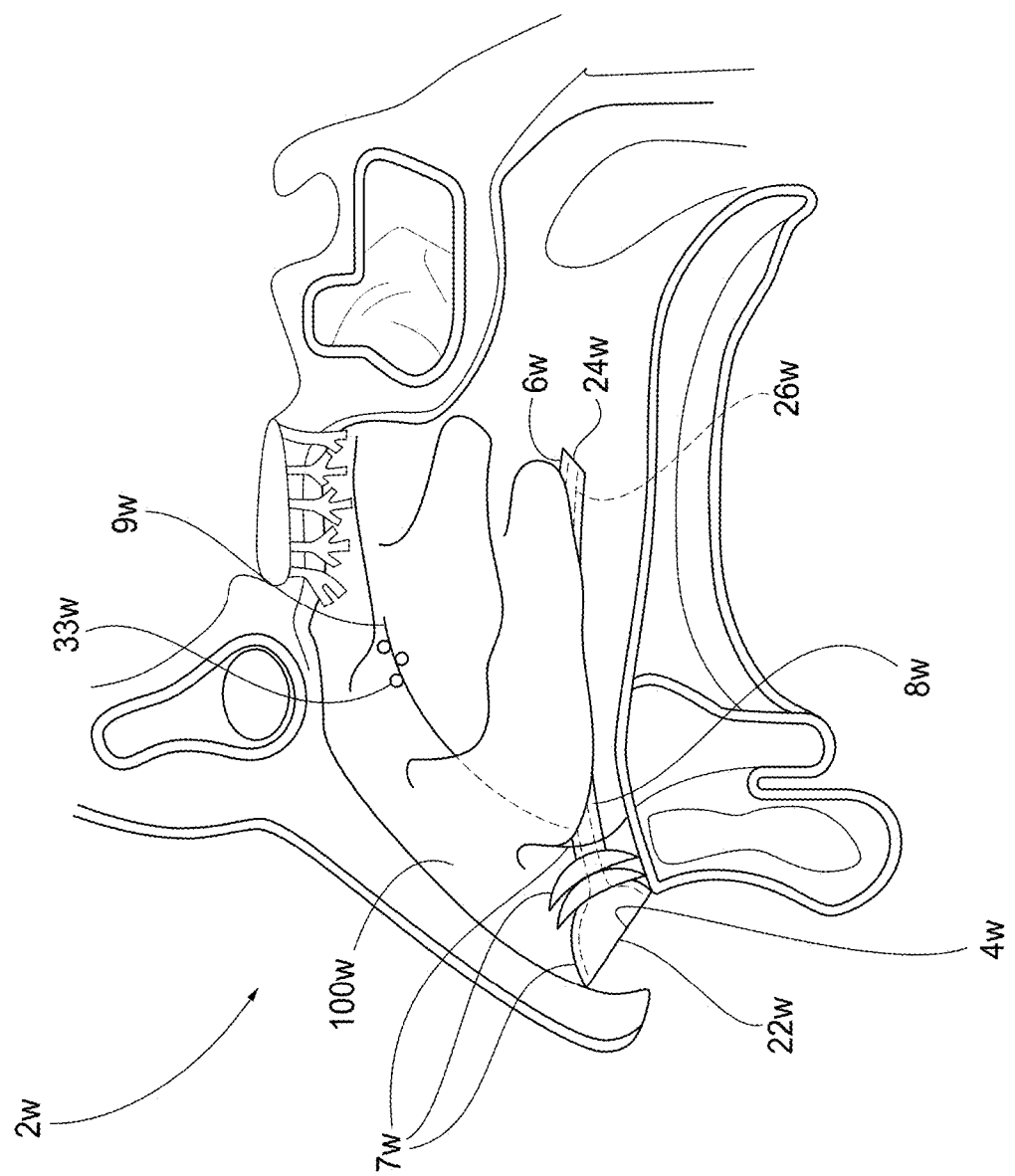
FIG. 26 is a side elevated view of a nasal insert contained within a nasal cavity made in accordance with the present invention.

FIG. 26 shows a nasal insert 2*w* inside of nasal cavity 100*w*, as described above. Nasal insert 2*w* includes a body 8*w* that may be compressible. Body 8*w* may include an inner surface(s) 4*w* and an outer surface(s) 6*w*. The inner surface(s) 4*w* of nasal insert body 8*w* defines an air passageway(s) 26*w*. Nasal insert 2*w* includes seals 7*w*, a proximate opening 22*w*, and a distal opening 24*w*. Nasal insert 2*w* may additionally include a thread-like structure 9*w*, which include sacs 33*w* for medicament or other treatment. Additional thread-like structures 9'*w* (not shown) may also be included.

Figure 27:
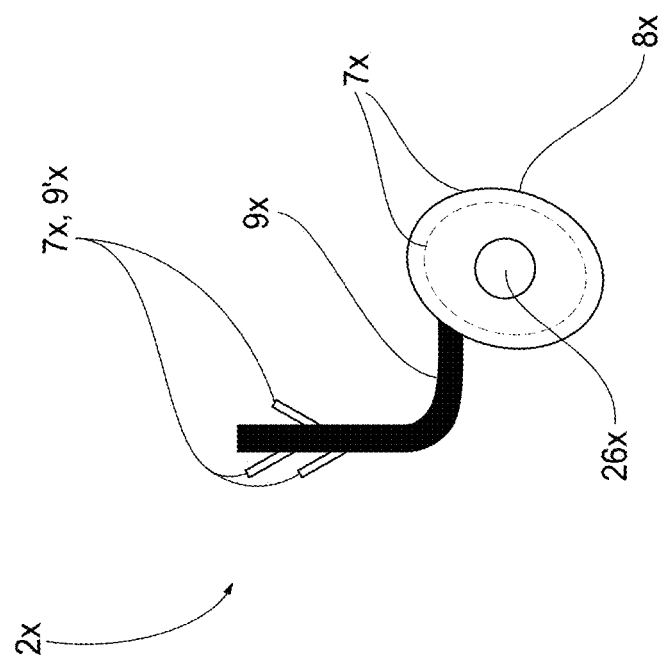
FIG. 27 is a front elevated view of a nasal insert made in accordance with the present invention.

FIG. 27 shows a nasal insert 2*x* including a body 8*x* that may be compressible. Body 8*x* includes a passageway 26*x* and seals 7*x*. Body 8*x* may also include a non-pipe, thread-like structure 9*x* (that may be changed to include a passageway), wherein the thread-like structure 9*x* may include additional thread-like structures 9'*x* or seals 7*x*.

Figure 28:
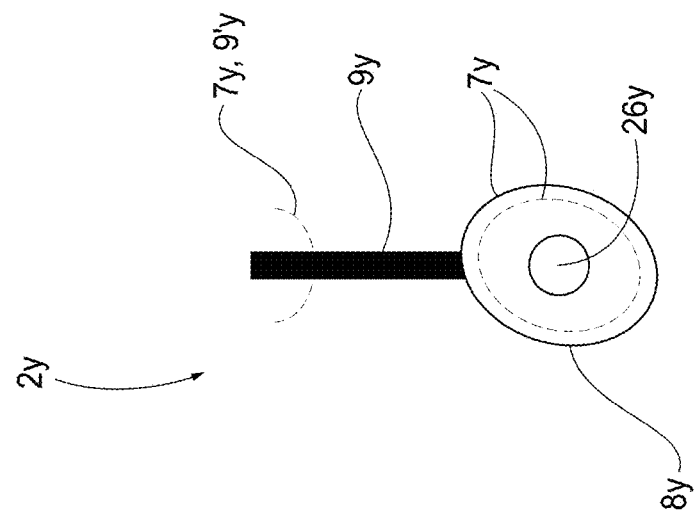
FIG. 28 is a front elevated view of a different embodiment of the nasal insert shown in FIG. 29.

FIG. 28 shows a nasal insert 2*y* including a body 8*y* that may be compressible. Body 8*y* includes a passageway 26*y* and seals 7*y*. Body 8*y* may also include a non-pipe thread-like structure 9*y* (that me be changed to a pipe with air passageway), wherein the thread-like structure 9*y* may include additional thread-like structures 9'*y* or seals 7*y* (both shown in phantom).

Figure 29:
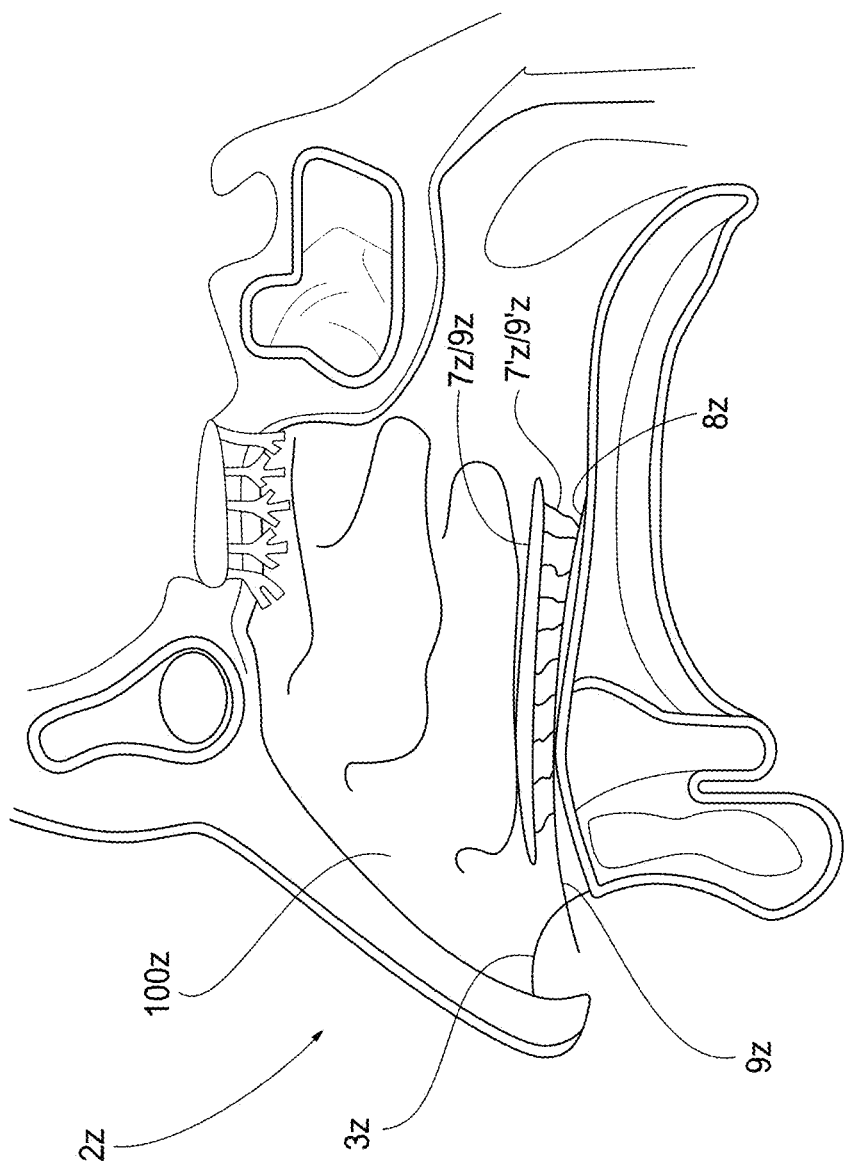
FIG. 29 is a side elevated view of an insert positioned within the nasal cavity made in accordance with the present invention.

FIG. 29 shows a nasal insert 2*z* inside of nasal cavity 100*z*. Nasal insert 2*z* includes a body 8*z* that may be compressible. Nasal insert 2*z* includes hooks 3*z*, which attach to the nasal cavity, a thread-like structure 9*z*, which has additional spring-like connecting member(s) 7'*z*, which connect to a large seal 7*z* that can act as delivering member as well. The thread-like structure 9*z* and spring-like/string-like connecting members (which may have spring-like functionality) 7'*z* may additionally include medicament also the connecting members can consist of one "sheet like"/'thread-like' or other connecting member. The large seal 7*z* helps divide the nasal cavity to different treatment areas: above and below it. It can prevent medicament from reaching the upper part of the nasal cavity Or it can deliver a treatment to the upper part while preventing it from the lower, or it can provide different treatments to the different areas. It may serve as a seal or a membrane.

Figure 30:
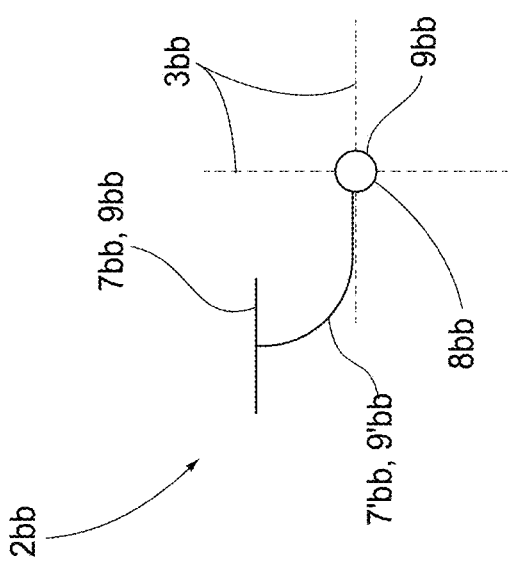
FIG. 30 is a front elevated view of an insert made in accordance with the present invention.

FIG. 30 shows a nasal insert 2*bb*. Which is similar to 2*z*. Nasal insert 2*bb* includes a body 8*bb* that may be compressible. Nasal insert 2*bb* includes hooks 3*bb*, a thread-like structure 9*bb*, which has additional string-like connecting members 7'*bb*, which connect to a large seal 7*bb*.

Figure 31:
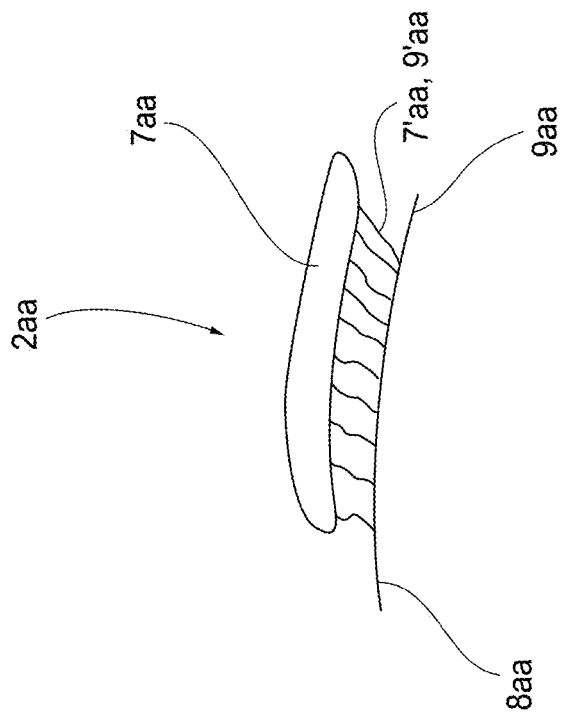
FIG. 31 is a side elevated view of an insert made in accordance with the present invention.

FIG. 31 shows a nasal insert 2*aa*. Nasal insert 2*aa* includes a body 8*aa* that may be compressible. Nasal insert 2*aa* includes a thread-like structure 9*aa*, which has additional string-like connecting members 7'*aa*, which connect to a large seal 7*aa*.

Figure 32:
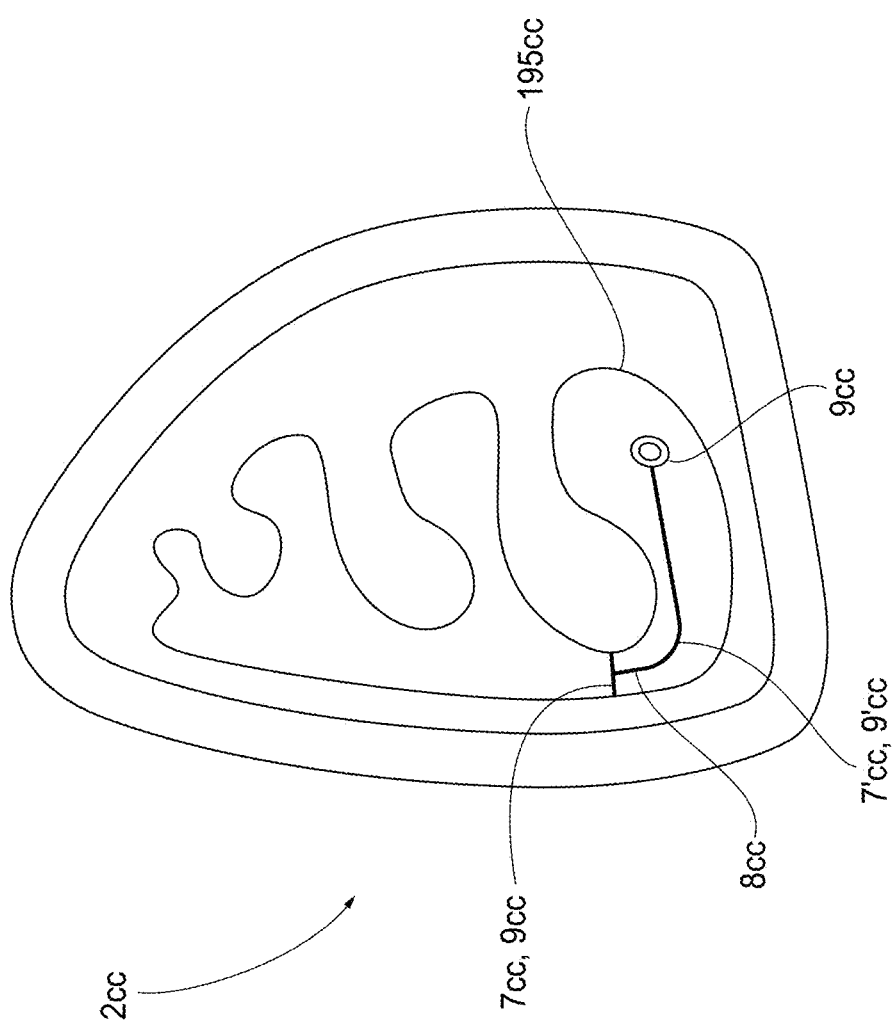
FIG. 32 is a front elevated view of an insert positioned in the nasal cavity made in accordance with the present invention.

FIG. 32 shows a nasal insert 2*cc* (which is similar to the nasal insert 2*bb*) inside the nasal cavity in a front cross-section view including a body 8*cc* that may be compressible. Nasal insert 2*cc* is placed against the septum and conchas/meatuses, between the nasal cavity roof and nasal cavity floor. Body 8*cc* may include a thread-like structure 9*cc* (which may or may not be solid, or include a pipe) and a seal 7*cc*; wherein the thread-like structure 9*cc* is situated within the inferior meatus 195*cc* (and can be situated in other meatuses or the septum air passageway without limitations and all according to the specific need). Body 8*cc* may also include additional thread-like 9'*cc* or seal structures 7'*cc*.

Figure 34:
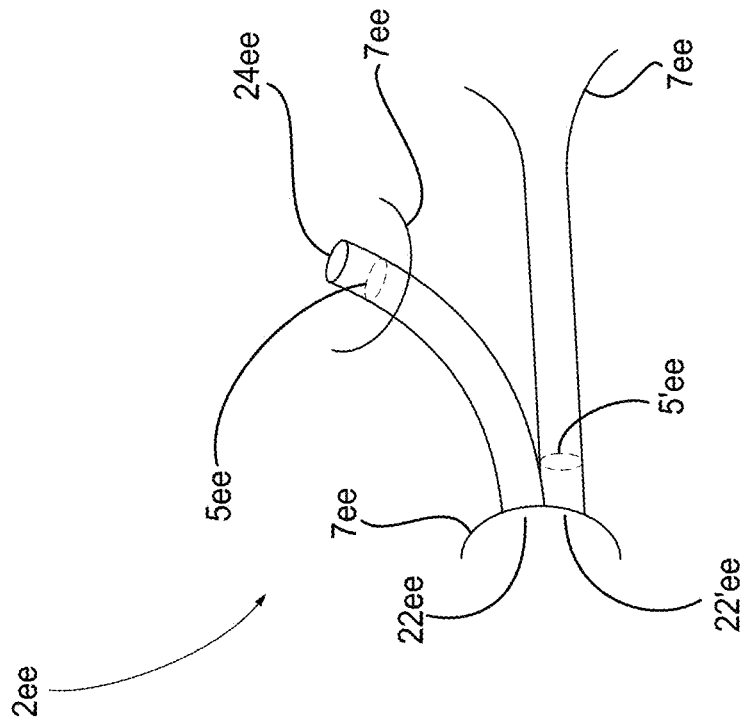
FIG. 34 is a side elevated view an insert made in accordance with the present invention.
Figure 33:
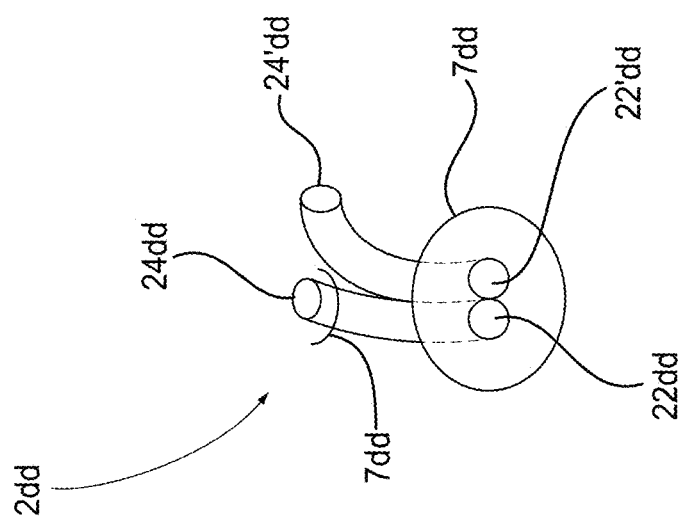
FIG. 33 is a front elevated view of an insert made in accordance with the present invention.

FIG. 33 shows a front view of a nasal insert 2*dd*. Nasal insert 2*dd* includes two passageways 24*dd* and 24'*dd*. Passageways 24*dd* and 24'*dd* have proximate ends 22*dd* and 22'*dd*, respectively. Nasal insert may also have seals 7*dd* and 7'*dd*. Each passageway has a valve 5'*ee* and 5*ee*, the number of passageways, ends, valves or seals is not meant to be limiting FIG. 34 shows a side view of a nasal insert 2*ee*. Nasal insert 2*ee* includes two passageways 24*ee* and 24'*ee*. Passageways 24*ee* and 24'*ee* have proximate ends 22*ee* and 22'*ee*, respectively. Nasal insert may also have seals 7*ee* at one end or both the proximate and distal ends. This embodiment and 33 demonstrate 2 passageways each having 2 ends with no "fluid" communication between passageways, but it is here clarified that the number of passageways and end and connection between them etc. is not meant to be limiting and any other combination may be implemented according to the specific need.

The nasal insert body may also include thread(s)/branch(es) or "spread sheets"/"leaf" like element 9*m* (see for instance, nasal body 8*m* of FIG. 16), meant to aid with delivering the treatment to the target area.

In addition, nasal insert body or any part of it may serve as or have special designated sealing/blocking/filtering/reducing/directing member(s) element(s) aimed to manage control and direct air/particles/signals/molecules/bacteria/treatment/etc. flow/reach etc., to bring them to desired area and/or to prevent them from specific areas. See for instance, sealing element 7*k* in FIG. 12.

Also nasal body or any part of it may further include membrane(s), filter(s) or valve(s) meant to improve and enhance the treatment and the capabilities of the device to better achieve the desired result, and also hold fast(s)/hook(s) to better secure the device in position. See for instance, insert body 8*j* of FIG. 11 showing valve 5*j* and hook 3*n* of FIG. 17.

In general all types of embodiments may have seals/blockers, membrane(s), open(s), filter(s), valve(s), air/treatment/particles/signals/hormones/molecules/substances/drug/other passageway(s), thread(s)/branch(s), sheet like element(s), hook(s), membrane(s) etc. The location, shape, structure and number of them is not meant to be limiting as many embodiments are possible. Also their role may include additional purpose—for example: the seal(s) may be used also to delivery of the treatment or absorbing, or may serve as a holdfast and others, in addition to or instead of blocking/directing. Also it is clarified that the nasal body itself may serve as such elements (seals, leafs, membranes, hooks, etc.) without having them being separated defined parts. For example nasal body can serve as the holdfast and secure the nasal insert in place, or it can create the required seal without having a separated sealing member(s).

In general, nasal insert body, and all its related element(s) as exist in the specific embodiment, may assume the shape of the nasal cavity, which may be different from its original shape. For example: outside of the nose the nasal insert air passageway's cross section may be an oval shape (or other), and while in the nose the nasal insert air passageway may be more bean-like or a smooth "L" shape or other suitable shape, the exact shape is not meant to be limiting as other shapes may suit for the required purposes. Or for another example: the shape of the passageway itself may be straight line outside the nose and in the nose it may curve to better adapt the cavity, same goes for any other element of the device. Also there is no limitation regarding the length shape, cross section thickness or any other parameters of the passageway (or other part) outside the nose or inside it. Also, because the nose conchas may be periodically expanding and shrinking as the user breathes and as the regular cycle of nasal cavity, the nasal insert body, and its elements accordingly, are flexible enough to change their shape accordingly. Nasal insert body will be rigid enough not to collapse and will maintain an open airway if the specific embodiment includes an air passageway that is needed to stay open all time. The ability of the nasal insert body to compress and expand also minimizes the pressure against the nasal mucosa, providing comfort. Also the ability to compress and then return to its shape allows smooth insertion and positioning in the required location in the nasal cavity. The expansion may occur simply upon releasing the pressure, or due to nose temperature/humidity, or by applying some material to the device—once in the nasal cavity or at any other relevant time. The expansion trigger and mechanism is not meant to be limiting as enormous amount of methods may be applicable for achieving it. Even so, it is clarified that the compression/expansion ability is not a must as in some cases it will not be required in order to achieve the device's purpose. The nasal insert body may be flexible to adapt to the specific shape of the nasal cavity allowing reach and adaptation to the complex nasal shape while minimizing pressure over the nasal internal mucosa through the periodical expansion and reduction of the conchas. The shape and size of the nasal insert body and any part of it are non-limiting and can vary as other shapes and sizes can be used having similar effects including round, bean, "L" shape, convex, straight, rectangular, curved, tapered, bulbous, leaf, sheet, thread many odd shapes or others.

The nasal insert body of FIGS. 1-34 may include air/treatment/other passageway(s). The passageway(s) that exists in part of the embodiments may begin at the upstream opening(s) (also referred to herein as proximate opening/end) and continuously extends through the nasal cavity to the distal opening(s) (also referred to herein as distal opening/end). For example (non-limiting), see FIG. 1 showing passageway 26 that begins at the upstream opening 22 and extending through the nasal cavity to the distal opening 24. Also it can be located differently in the device or in the cavity all according to the specific need and embodiment. By moving through air passageway(s) the air/treatment/molecules/particles/signals/other are conducted to the relevant area or away from a specific area as required for the treatment. For example in FIG. 16 the air flow/etc. is directed to the posterior nasal cavity bypassing the olfactory region 150*m* located in the uppermost part of the nasal cavity and being avoided from other areas such as the middle meatus, sinus' opening and most of the nasal lining. Nasal insert body 8*m* can also have a shortened air passageway (shown in phantom in FIG. 16) in which case air may still be bypassing the olfactory region 150*m* because it is directed to pass but yet it will come in contact with major part of the nasal lining. On another embodiment shown on FIGS. 1 and 6, air passageways 26 and 26*e*, respectively, directs air flow/treatment/etc. to olfactory. In another example, shown in FIG. 25, passageway 26*v* is position in the middle meatus. In this case it may deliver treatment to the middle concha, or to the sinus in the middle meatus, or to other purpose, or direct air to bypass olfactory, or direct air to bypass inferior meatus, or sinus opening and middle meatus if having it longer—which may be provided with a treatment at that time by the thread 9'*v* (marked in phantom). Of course the treatment(s) could be provided with any part of the device for example the outer surface pf the passageway, the seals, inner surface etc. without limitation. FIG. 11 provides example to a nasal insert having more than one passageways (marked as 26*j* and 26'*j*-phantom).

The number, length, shape, cross section shapes etc. of air passageway(s) is not meant to be limiting and will be set specifically as will be relevant for each implementation. Air/treatment/other passageway(s) may exist in different locations in different possible embodiments. This embodiment may be used for example (non-limiting) for providing treatment to two/few areas—for example olfactory and middle meatus/sinus opening. It can be the same or different treatment(s). The amount of the passageways and treatments is not meant to be limited. Also a combination of delivery via thread(s)/branch(es) and passageway(s), and sealing(s) body etc. may be leveraged according to the specific treatment(s).

FIG. 11 also illustrates another non-limiting example for having several passageways would be: leveraging all incoming air/particle(s)/signal(s)/treatment(s)/etc. flow to deliver the treatment via passageway 26'*j*, while also preventing out going stream from traveling via passageway 26'*j*. This may be achieved by adding for example one directional valve 5*j* to passageway 26*j* in a location for example right after (deeper) the split of passageway 26'*j* and 26*j* and possible additional valve 5'*j* to passageway 26'*j*, for example near the distal end 24'*j*. Valve 5*j* may, in this example, enable flow only outwards while preventing inwards (into nasal cavity beyond the valve 5*j*) flow via it. This will direct all inward flow to move via passageway 26'*j* and will assist in delivering treatment thereto. Having passageway 26*j* enabling flow outwards via the valve 5*j*, while having passageway 26'*j* is not enabling out flow due to valve 5'*j*, will result in having outward flow moving out via this passageway 26*j*, and by that preventing the flow outwards that could have been occur via passageway 26'*j*. Also, passageway 26*j* may serve for example for cleaning and then drainage of the sinus opening. Such flow control may, instead/or in addition to it, be achieved also by different sealing elements as was explained in other embodiments, and by other means.

Another non-limiting example for delivering dedicated treatment while using passageway(s) 26*l* is provided in FIG. 15: in this embodiment a treatment can be given through the passageway to the throat/trachea/lungs- and being prevented from the nasal cavity lining, from olfactory etc. the passageway in this embodiment continues beyond the nasal cavity and can continue down to pharynx or further. This embodiment may have or not have tail seal and other elements.

FIG. 12 (and also in FIG. 32) provide non-limiting examples for demonstrating that passageway(s) 26*k* may be created not only solely by the inner surface(s) 4*k* of the device, but also by a cooperation of the device and the nasal cavity organs. For example (non-limiting)—as shown in FIG. 12 (and also in FIG. 32)—by a combination of the nasal insert body 8*k* or part of it (for example the inner surface 4*k* of the nasal device body 8*k*) and the nasal floor serving as a part of the air passageway. Based on this principle, a passageway can be created in any desired location in the nasal cavity. Also a passageway(s) can be established by a combination of the apparatus body with another element, such as, for example, a sealing member, an active ingredient, external applicator or tool etc.

The passageway may also be used for filtering ingredients/molecules/signals etc. For instance, air or other substances may be filtered. For example, the passageway allows exhaled air to flow through it, but filters the active ingredient in order to keep it in the nasal cavity. Or a filter located in a passageway that assist the delivery. In this case, the filter will be used for filtering the inhaled air in order to prevent specific type of particles from being involved in the delivery or reaching the target area for the treatment. Also irritating particles may be prevented.

Depending on whether a seal is conducted and what is the type of such seal, passageway(s) may or may not serve as the only way out or in of the nasal cavity for exhaled air/particles/etc. moving outwards and for incoming flow. For example a possible seal can be based on sealing members that are directing incoming environmental air and signals to enter the nasal cavity only via a passageway and be directed by passageway accordingly. These sealing members may also prevent air/molecules/etc. from moving around passageways of the way out. On the other hand, those seals can be one-directional collapsible seals—meaning they will collapse and will not prevent particles movement out and by that, or by any other relevant means (for example not limited: filter, one directional filter capabilities. Membrane etc.) will enable such flow also regardless of the passageway. Such seals of-course can control movement on the other way around-meaning enabling flow around the passageway on the way in to the nasal cavity and directing all outward movement to be only or mostly through passageway(s). In this case the passageway may as itself be in a shape or include elements that will reduce/prevent streaming in but will enable streaming out, for example by one directional valve, membrane, filter, tapered shape—more narrow near the nostril opening and wider deeper in the nasal cavity and many other possible implementations that can work. The management of the flow shall be conducted according to the relevant treatment. For example if we would like to leverage/manipulate/use internal signals which are part of the outgoing flow—we may direct it to the relevant area. If we wish to avoid/minimize intranasal air circulation, we may create a seal that will minimize it or if we wish not to have such internal inputs to olfactory or other organs we can then direct outgoing and/or incoming flow to move only or almost only in defined channels and be prevented from others.

The passageway(s) may contain the releasable/treatment material (also referred to herein as "material able to coact with the body" or as a "component able to create the required effect" of the nasal insert. That material can be present at the passageway prior to insertion, or can be applied to it before or right after insertion, or the material may be inserted and delivered after the apparatus is in its position within the nasal cavity. The passageway can include treatment inside of it to be delivered to a destination located in most cases at the end of the passageway, or it can be on the outer surface of it to be delivered to the nasal mucosa or areas in which the passageway is resting against. For example a treatment on the outer surface may aid in reducing nasal sensitivity due to allergies or congestion, and the passageway itself may aid reduce the contact of irritating airborne or other particles/materials from contacting the mucosa, and by that reduce and ease allergies.

The apparatuses provided herein may have one or more sealing/directing/blocking/barrier(s)/inhibiting/reducing members extending from the nasal insert body, or from the elongated, flexible, non-collapsible member(s), the branch(s)/thread(s), "leaf(s)" or any other part of the nasal inserts. The sealing member may be in various shapes, depending on the location and the need. The shape of the sealing member is not meant to be limiting and can be of any shape that will support its functionality in the required location. For instance, it may have an oval shape, a leaf shape, or a circular shape or any other shape as relevant. For example: FIG. 20 demonstrate sealing member(s) extending from the "sheet"/"leaf" (we are relating here to the uppermost seal market with phantom) and meant to aid with the treatment delivery and maintain it at the area of the nasal roof—reducing its spread to the rest of the nasal cavity. This seal may also have absorbing/filtering characteristics meant to assist in preventing/reducing the reach of the treatment to the rest of the nasal cavity. For example to reduce the reach of the treatment to the nasal mucosa and from there to blood stream. FIG. 11 demonstrate several seals: two seals are located at the vestibule one near the nostril opening and one inside the nasal vestibule, and one deeper after nasal valve. These seals direct the air/particles/etc. to the passageway 26*j* and may have other uses as well. In FIG. 25 there are two seals in the vestibule directing air to passageway 26*v* (and may have other uses), and additional seal 7*v* and 7'*v* may be present and extending from the upper thread/branch 9*v* and may help to keep the treatment in proximity to the target area and prevent its spread, and/or to assist delivering the treatment to a broader area or to any other relevant role. FIG. 11 as mentioned demonstrate additional seals extending from outer surface 6*j* of the nasal insert body 8*j*, and FIG. 15 demonstrate a seal conducted by the nasal insert body 8*l* (marked on body 8*l* as 7*l*), and another seal 7'*l* located at the tail. FIGS. 29-32 demonstrate a seal that is connected to a delivery thread/branch 9*z*, 9*bb*, 9*aa*, 9*cc* by a connecting part 7'*z*, 7'*bb*, 7'*aa*, 7'*cc*. This connecting part may be also used for delivery of treatment(s), and may be in a shape of a surface, and or threads and any other relevant shape. In this embodiment the seal is conducted in cooperation of the seal 7*z*, 7*bb*, 7*aa*, 7*cc* with the lower concha and the nasal septum. The amount, type, connecting form, shape, thickness, material, location, capabilities (such as—not limiting) absorption, filtering, expansion, elasticity, plasticity etc.) locations and other characteristics of sealing member(s), and of other nasal insert's elements are not meant to be limiting. Also the sealing/reducing/inhibiting/filtering/etc. affect can be achieved by using specific relevant materials for the nasal insert body, or for a layer of it, or for the sealing member(s) or part/layer of it or to other relevant part of the nasal inserts. For example by using materials that expand and absorb once in contact with fluids or other substances as may be relevant for the device, or by using materials/structures that trap specific type of molecules/cells and enable the movement of others, or by any other possible mean that currently exist or be become available in the future.

Sealing member(s), as indicated, are used for directing air/particle(s)/substance(s)/signal(s)/etc. movement in the nasal cavity, directing a specific drug, treatment or other material inside the nasal cavity, or to block, prevent, or reduce the amount of air, drug, or other material from reaching specific area(s) in the nasal cavity. The sealing member can be located anywhere on the outer surface. In specific embodiments, if a passageway(s) exists, then the sealing member(s) can be located in the passageway. The nasal apparatus body itself can serve as a sealing member without having any additional sealing member(s) extending inside or outside of it.

The sealing member(s) may also be used for filtering ingredients/particle(s)/etc. For instance, drug or hormone or other substances may be filtered and can be prevented by that from a specific area, or may reach a specific areas after being filtered from other ingredients. The filtration can be based on the size/structure of molecules, or of other characteristics such as polarity, or other as may be relevant for the application and available to use that time. The filter material, can be such as, but not limited to, polypropylene fibers, medical plastic, or silicon materials that are widely used in air-conditioning systems, infusion systems, and/or respiratory systems to prevent the transmission and spread of bacteria. These are only exemplary materials and any relevant material that will prevent the of transmission and spread of bacteria, or other substances/signals/etc. or enable the movement of air/other material back down to nasal cavity through it, but will decrease the amount of the drug, odor or other desired component, may be employed. The type and characteristics of filtering shall be defined according to the needs at a specific treatment or condition and are not meant to be limiting.

The sealing member(s) may be in a closed/collapsed form during the insertion and can be opened afterwards once located in the nasal cavity. The opening of the sealing/directing member can occur by many means, for example, but not limited to, as a result of the moisture within the nasal cavity, and/or, intra-nasal temperature, for example, the sealing/directing member opens because of the high humidity within the nasal cavity. Alternatively, the sealing/directing member may be spring like, and open based on pressure, or lack thereof. In another example, it can be in a vacuum state through insertion. Once inserted, can be filled with air, or for example, by absorbing internal or external fluids, and therefore, releasing the vacuum state. Alternatively, by inflating, due to a reaction to the presence of specific cells (for example, specific hormone, infection), or any other relevant reaction. In general, the seal may be in a "compressed" state when outside of the nasal cavity, but may be "released" when inserted into a nasal cavity.

The nasal insert body may further include an enlarged bulbous-shaped head/proximate end (see for instance, FIG. 26 with nasal insert body 8*w*). The shape of the proximate end is non-limiting, as other shapes can also be used according to the specific need, such as for example, a pear, oval, funnel, curved, straight, triangular, rectangular, or rounded shape, and also the nasal insert may be without any specific shape or very limited for example as shown in FIG. 29. The nasal insert proximate end may be designed to produce a seal and/or to serve as a hook, but other parts of the nasal insert body may serve for such purposes if needed. The nasal insert body may also not include a specific enlarged shape a the proximate end, see for example FIG. 17.

The nasal insert body may be flexible to adapt to the specific shape of the nasal cavity if this is required for the specific application and embodiment. The nasal insert body further extends into the nasal cavity to one or several directions according to the specific application and embodiment. For example in embodiment FIG. 16 the nasal insert body 8*m* extends towards 2 main directions: 1. It extends through the inferior meatus and towards the nasopharynx with the air passageway 26*m* (partially market in phantom), and it extends along the septum and up to nasal roof and olfactory with the "sheet"/"leaf" through delivery element 9*m*, shown as 26'*m*. In addition, each extending part can include a tapered tail or other shaped end according to the needs without limitation. The nasal insert body may be flexible to adapt to the specific shape of the nasal cavity allowing reach and adaptation to the complex nasal shape while minimizing pressure over the nasal internal mucosa through the periodical expansion and reduction of the conchas.

Further, the nasal insert body can also have a slanted or tapered or other tail or a bulbous shaped tail as shown in FIG. 15, or any other shape and characteristics as relevant.

In a different another example shown in FIG. 11, when the nasal insert body 8*j* is inserted into the nasal cavity 100*j*, the nasal insert body 8*j* can be positioned inside the nasal cavity 100*j* and in nasal vestibule, so that the nasal insert body rests fully, and/or partially against a portion of the nasal cavity, forming a seal between the nasal insert body 8*j* and the nasal walls with sealing member that in this case is located right at the nasal valve (in this embodiment can be located in the nasal vestibule at the nasal valve, or right after the nasal valve-in the nasal cavity from nasal floor to nasal roof—right before the conchas start, and allowing air to pass through air passageway 26*j* while blocking air from passing around it. The exact location and shape/form of the sealing member(s) (or sealing part of nasal insert body 8*j*) is not meant to be limiting as many embodiment can work.

The apparatuses described herein can be made of smooth, yet rigid material, to avoid discomfort or injury while enabling the insertion of the apparatus into the nasal cavity all the way to the target area of treatment without collapsing. This may be achieved by using one material or more materials, in a suitable combination. Examples of some materials are listed below. For example, a combination of materials that provide a rigid internal "bone"-like structure covered with softer material. For example, the "bone"-like material can be made of Teflon or from plastic and the soft material can be made from rubber, soft plastic. In other words, the device shall be made from a soft, flexible material, that yet has sufficient rigidity, in order to enable smooth and pleasant insertion into the nasal cavity. Further, the nasal insert device may have the characteristic of being easily adapted and molded to the nasal cavity's unique, gentle structure and tissue, while maintaining the device's unique shape and delivery capabilities. The outer surface of the device can be soft enough to be inserted and to be in touch and direct contact with the nasal tissue, while the internal part may provide the rigidity necessary to maintain the overall structure of the nasal insert device. The right composition of rigidity together with flexibility and softness may be achieved in many other ways as well, and is not limited to the above. For example it can be achieved by having different thicknesses or, some layers etc. Example for suitable materials include: FDA approved carbon based substances, (e.g. polyglycol-glycerol-sebacate)), a shape-memory polymer (SMP) (e.g. PET cross linked with Glycerol/dimethyl 5-sulfoisophthalate), or silicon based materials (e.g. polydimethylsiloxane), these materials may or may not be biodegradable. Or suitable plastics such as TPE, SEBS or others. Additionally metals, either elementary, as an alloy, compounded or metal ions may be used, these metals may include, but are not limited to, titanium, stainless steel, platinum, iridium. The materials are not meant to be limiting as any material that is suitable can be used for it, existing or future developed material.

Also, these and other substances may be also used in combination with (or as) powder and/or as nanoparticles embedded in the matrix of the device material or as a coat to the device or part of it in order to facilitate the functionality of the device or to provide it with additional functionality, or may be provided or connected in other relevant manner (see for instance, FIG. 1, wherein "N" notes incorporation of nanoparticles in the matrix of the device). This may be done with any of the inserts that are made in accordance with the present invention. For example, nanoparticles may be embedded in the branches/threads 9*v*/9'*v* or seals 7*v*/7'*v* of FIG. 25. Insertion of insert 2*v* into the nasal cavity promotes the release of the nanoparticles embedded in branches 9*v*/9'*v* to reach the target area to treat in the nasal cavity, or in "sheet"/"leaf" like 9*m* of FIG. 16, or in possible thread(s) for example 9*v*/9'*v* in FIG. 25, or in passageway(s) for example 26*j* of embodiment FIG. 11, or in different surfaces, for example the outer surface of several of the figures. Such functionality may be, but not limited to, antimicrobial, nasal targeted drug release etc. Such composite material may be, but is not limited to, sintered hydroxyapatite/silicone composite, hyaluronic acid and polyethylene glycol. Additional materials can be used for connecting the device, or specific element of it, to body tissue if such function is required, or for connecting different parts, layers, materials of the device to one another (for example sealing member(s) or branche(s) as required for the specific functionality). These additional materials may include, but are not limited to, bioadhesives, such as, fibrin glue, cryoprecipitate glue, containing gelatin-resorcinol-formaldehyde-glutaraldehyde, high molecular weight polydimethylsiloxane adhesives and other suitable equivalent materials. Biodegradable materials may additionally be used. Suitable materials include, for example, but are not limited to: polycaprolactone, poly(ethylene glycol), maltodextrin modified by fatty acids, silicone, Tygon®, hydro-gels, cotton, Merocell®, silicon, polyurethanes, polyvinylchloride, dimethylpolysiloxan, silicic acid, azodiacarbonamide, reticulated foam, polyethers, polyesters, polysiloxanes, polycarbonate, polyolefins, polybutyrate, polyethylene teraphtalate (PET), Polymides, polyethylene glycol, activated carbon, biodegradable material, anti-microbial agents, plastic materials, silver, bamboo, antimony, aluminum, metal materials, polymers, wood, resins, carbon based materials, carbon nanotubes (CNT), esters.

The nasal insert body or part of it (for example the sealing member, or branch) may consist of one layer or more with no limitation. Further, the apparatus body, or part of it, may also be made from a material that will enable the user to adapt its shape (like in plasticine work) to fully suit a specific anatomy or use, for example to bend a specific portion, or to have a specific portion be narrow, while preserving the overall shape of the apparatus. Additional materials that the apparatus may include are mesoporous materials, allowing for drug delivery of any type, amino-acid based drug delivery systems, other relevant drug delivery technologies, materials and mechanism. Further, the apparatus may include several releasable materials to be released each at specific times. In one example, the apparatus may include an anaesthetization material, such as, a combination of lidocaine and epinephrine, or any other acceptable anaesthetization. Such materials may be also released during the entire stay of the device in the nasal cavity, while other materials are being released at specific time/s or continually.

One possible feature of the invention is to provide the device, or part of the device, with a drug, odor, or suitable therapeutic agent. In other words, the apparatuses provided herein may include one or more releasable ingredient(s). The releasable ingredient(s), also referred to herein as active agent, active ingredient, or therapeutic agent, can be of any kind, suitable for any purpose, in any suitable form. The releasable ingredient may be, for example, but not limited to: drug, medicine, vaccination, physiological water, watery material, oily material, anti-bacterial, gas, solid, liquid, paste, ointment, anaesthetization, medical soap, hormone(s), agonists, antagonists, peptides, enzymes, odors, materials to shrink nasal mucus/polyps/tumor(s), sanitization and antisepsis, proteins and other biological/genetic molecules, gene therapy, cell targeted therapy, immunotherapy, chemotherapy, electric signals/therapy, radiation based treatment, light therapy, and any other relevant existing or future, molecule/treatment/other.

The releasable ingredient may be provided in combination with other diagnostic/treatment methods and/or devices, in order to enhance diagnoses and treatment of ailments. For example, the releasable ingredients may include elements that allow for use in diagnostic/treatment methods, such as intra-body imaging, or various relevant nanotechnology-related. Use of the herein devices may allow for more efficient diagnoses and/or treatment of ailments when used in combination with various other diagnostic/treatment methods. For example, the releasable ingredient may be provided via a transdermal materials based technology, a protein-based therapy, a vaccine therapy, via electric, ultrasonic, or laser-based technologies, or any other relevant technology or method. Alternatively, as indicated, the herein provided devices may be coupled with mechanisms for providing a treatment, such as, some remote controlled mechanism, mechanisms that have recording capability or transmission capabilities, or any other type of material or technology that may be suitable for such implementation. Further, the herein provided devices may be coupled with any combination of materials and technologies, in the form of liquid or solid or gas or light or power or other or combination of all or part of the above or any other technology or capability.

In some non-limiting examples, the nasal insert may include anaesthetization material and a substance that shrinks the mucus, in order to ease the insertion of the nasal insert and/or additionally, to maintain the position of the nasal insert within sensitive areas of the nasal cavity. Sensitive areas of the nasal cavity include areas, such as, the superior meatus. The nasal insert may additionally contain for example the hormone, Leptin to be released once in position, near olfactory region. The Leptin may be delivered in a form of targeted nanomedicine or in other form, in order to promote targeting of the leptin to the leptin receptors in the olfactory region, and also in the brain, through the trigeminal nerve or blood system or directly through olfactory. The Leptin can also be directed to targeted peripheral body organs/cells using nanomedicine technology. It can be, for example, transmitted through absorption to the blood system or via transdermal technology, through simple contact through nasal lining. Specifically, in one non-limiting embodiment, the active ingredient may be provided in the form of gas, which will be absorbed through the nasal lining.

As discussed, the nasal insert can include the releasable ingredient. The releasable ingredient may be impregnated in the material in of the nasal insert homogeny or non-homogeny manner, it may be located in sacks/containers, anywhere on the device, for example (non-limiting): inside the material, or layer/layers of it, or on the body surface of it, may be located only on the branches members or inside of it or at the most remote point of them, in proximity to the TA or on the external walls of the device, or in the internal passage of the device, on the sealing members, or it may be located in certain portions of the nasal insert. It in can be located on the outer layer of it or inner or can be a layer of the materials of the nasal insert. Another option is that the nasal insert body itself or part of it will be made of the releasable/active material. Also several therapeutic solutions for same or different diseases/conditions may be provided by same device. Additional option is that the nasal insert will be vehicle or the transmitter of an external source of active ingredient.

As described herein, the drug or treatment relating to a specific condition(s), purpose, and/or a specific ailment, may be provided by a variety of methods. The following provide additional non-limiting examples.

In some embodiments, a releasable, therapeutic, ingredient may be coated on any part of the nasal insert device, may be integrated into the material of the device, or may be provided/connected differently. Alternatively, it can be applied to portions of the nasal insert device through an external applicator, or the device can be soaked in a solution prior to insertion or any other means and methods can be used for having the device carrying and delivering a required substance material. The required substance may be in any relevant form, for example solid, liquid, ointment, gas etc. and may be located directly or indirectly on the nasal insert device (see discussion above with respect to releasable/therapeutic agents). Also, the therapeutic agent may impregnated in the nasal insert device. The therapeutic agent may be released from the nasal insert device as a consequence of some intra-nasal condition, trigger, or other reaction. For example, the temperature in the nasal cavity, and/or moisture or the presence of an enzyme, hormone, bacteria etc. in the nasal cavity may promote the release of the therapeutic agent. Other initiators for release can be applicable, intra-nasal, external and others. some examples for that may be:

external pressure applied to the nose, ultrasound, radiation, radio, electromagnetic, applying initiating material to the nasal, and any other method as will be relevant. Also, the active ingredient/s may be contained in a small container/s, sack/s, or cover on the nasal insert device. The small container, sack, or cover may be made from the same material of the device, optionally in a much thinner thickness. The small container, sack, or cover may alternatively be made from other material, for example, a material that can melt or disconnect due to temperature/humidity enzyme, bacteria and alike within the nasal cavity, or as a result of another mechanism internal or external that results in the release/activation of the active ingredient.

The container, sack, cover, or equivalent permits delivery of the drug in a variety of ways. For example, but not limited to the following: the container, sack, cover, or equivalent may contain small holes that expand due to intra-nasal temperature and/or moisture/humidity or due to other intra-nasal or external mechanism. As a result of the expanding, the drug/odor/therapeutic agent are released, allowing it to be delivered to the intended location. In another example, the sack, cover, impregnated etc. material or equivalent may contain a component, such as, for example, a biological, or a nano-technological component, that will cause the release of the material as a result of the reaction to a defined situation. For example, by reaction to the presence of specific cells, specific hormones, an infection or purulence, specific proteins, for example by using artificial nanodevices, such as biomolecular sensors and artificial cells or any other relevant reaction or in any other suitable manner, allowing the drug, odor, material alike to exit the sack/the device and be delivered. Alternatively, the container, sack, cover, or equivalent, or some part of it, may melt or open up, thus allowing for the release and delivery of the therapeutic agent. In another example, the sack, cover, or equivalent is made of a material that allows for controlled transdermal/trans-mucosal fast and slow release immediate or delayed or spread over time or at once, of the releasable substance, for example, Eluting Bandage. In another example, the container, sack, cover, or equivalent may be opened by the act of insertion of the device into the nasal cavity, or right before or right after the insertion. The drug, odor, or any therapeutic agent may be released all at once, gradually, or at specific intervals, depending on and according to the requirements of the specific ailment being treated. The drug, odor, or suitable therapeutic agent may reach its destination through inhalation/exhalation, by absorption, by dissolution, by direct needle-free transdermal solution such as the Eluting Bandage or other, by cell targeted technology, or by other means.

In another example, the device or part of it or a carrier of the therapeutic agent may be "glued" to the nasal cavity in the relevant area through use of bioadhesives, such as, fibrin glue, cryoprecipitate glue, containing gelatin-resorcinol-formaldehyde-glutaraldehyde, high molecular weight polydimethylsiloxane adhesives and/or other suitable equivalent materials. The device can deliver and connected the relevant part to the required location in the nasal cavity and then be removed—while the glued part stays in the nasal cavity. The device or part of it can then stay in the nasal cavity until they shall be removed or can be biodegradable.

Also it is important to emphasize that the apparatuses of this invention may act without having any active/releasable therapeutic ingredient. They can provide aid by acting purely based on their structure and mechanical characteristics.

The herein described apparatuses may additionally have an absorbing capability. Specifically, the apparatus of this invention can be used for opening, cleaning, draining, absorbing, or like functions, intranasal target areas or other areas. For example, reaching a sinus opening and delivering for example saline water thereto, or rather than saline, any other suitable, purification material, washing material, medication, or shrinking material such as adrenalin based materials to shrink the lining of the sinus opening in order to open it and drain it. Further, maintaining the nasal insert, which includes absorbing material, in position in order to absorb mucus, purulence, and or any other secreted substance; and additionally wherein the nasal insert includes material for cleaning, opening, removing (for example from sinus opening), enabling the drainage of the sinus or other relevant area and absorbing it or enabling its content to flow out to the nasal cavity, or for any other purpose. For example (non-limiting), the device may be made of, or include parts made of, but not limited to, polycaprolactone, poly(ethylene glycol), maltodextrin modified by fatty acids, silicone, Tygon®, hydro-gels, cotton, Merocell®, silicon, polyurethanes, polyvinylchloride, dimethylpolysiloxan, silicic acid, azodiacarbonamide, reticulated foam, polyethers, polyesters, polysiloxanes, polycarbonate, polyolefins, polybutyrate, polyethylene teraphtalate (PET), Polymides, polyethylene glycol, charcoal (activated carbon), biodegradable material, anti-microbial agents, plastic materials, silver, bamboo, antimony, aluminum, metal materials, polymers, wood, resins, carbon based materials, carbon nanotubes (CNT), esters.

The apparatuses of this invention may also include small camera with ability to transmit a picture. Such functionality may ease the navigation in the nasal cavity to reach the desired location and also may enable to better understand the exact status. This could replace or serve as or be an extension of the endoscope.

Examples for methods of use: the below detailed methods are few among endless possibilities of use and are provided here in order to a bit elaborate, clarify and demonstrate the some of the practical useful potential of use for the devices of this invention. These examples are not meant to be limiting in any manner.

To use the nasal inserts illustrated in FIGS. 25-32 and as was specifically adapted to this treatment and illustrated in FIG. 26. In this example Leptin hormone or agonist may be used combination with perfume odor to be the active ingredient. We may put the active ingredient in a humid-melted sacks that will be located at the remote end of thread $9w$ and marked as $33w$. Thread $9w$ enables the delivery to olfactory region as it located in the septum airway progressing up to olfactory. The apparatus further includes and air passageway $26w$ located in the inferior meatus and curved downward. The air passageway $26w$ of this embodiment is bypassing olfactory region. The apparatus further includes seals $7w$ at the nasal vestibule, nasal opening, a proximate end of the device and at the nasal valve. The TA (Target Area) are defined as the olfactory region-leptin receptors and the brain. Inserting the nasal device $2w$ into nasal cavity and positioning seal $7w$ at the nasal vestibule and in proximity to the nasal valve creating a seal and directing all inhaled and exhaled air to flow in and out of the nose via air passageway $26w$.

The seals of this embodiment leads to the formation of an airlock in the nasal cavity-marked as $7w$ in FIG. 26, reducing the circulation of air (from exhaled/outgoing signals) in the nasal cavity including near the olfactory. Passageway $26w$ and thread $9w$ are continuing beyond the nasal valve deep into the nasal cavity, where thread $9w$ is located at the air passageway near the septum—meaning continuing from the nasal valve deeper in the nasal cavity and then up, where its remote end is reaching the superior meatus in proximity to the olfactory region, and where the passageway 26w is resting in the inferior meatus bypassing olfactory region and most of the nasal cavity. Then, after nasal insert 2w is located in its position and being exposed to a certain level of humidity, the sacks 33w are opened and release the Leptin hormone/agonist and the perfume odor. The Leptin hormone/agonist is then connected to Leptin receptors in the olfactory and in the brain. By doing that we may promote satiation and inhibit/control eating since a satiation is sensed in the brain, and also the smelling threshold capacity is reduced. Even the satiated sensation on its own may promote weight loss. In addition, the perfume odor may mask and occupy the smelling sensors in olfactory region. Contributing to inhibiting the ability to smell environmental odors in addition to the environmental input blockage/reduction achieved by the sealing the directing the air by the air passageway. It is known that in some cases, when satiated the smelling identification capability is improved and may sometime lead to additional eating, but with using the perfume odor this can be prevented as well, leading both to satiation and to higher level of blockage of odor sensors in the olfactory to achieve better results. The seals 7w serves both as a hook and as a seal that causes the inhaled and exhaled air to move via the passageway 26w and reduces air circulation in the nasal cavity that may cause the active ingredients to spread and will lead to waste and to the reach of larger amount of active ingredients to different areas than the TA. This method can be used before eating, or during eating, or throughout the day, or several times/hours a day, or throughout a period. It can be used in both nasals—for example if external odors are to be prevented, or in one nasal. While using in nasal environmental odors and other inputs will be less prevented from olfactory then when using in both nostrils.

Another method of use, that can be combined in many treatments—including for example without limitation, with the Leptin based example herein above, but with many other treatments as well, whether including actual active ingredient or are based on the mechanical characteristics of the apparatus is as follows: as mentioned before, signals from both outside the body and inside the body are reaching olfactory and brain and affecting the management of processes and mechanisms of the body. In this example we would like to provide a non-limiting example for leveraging signals from inside the body in order to affect bodily processes. Enhancing the affect and effect of intra-bodily inputs may be achieved by "trapping" them or manipulating them and directing them to olfactory. (by manipulating them we can for non-limiting example filter them and direct only specific part of them to reach olfactory, or we may enhance them, or we may connect additional molecule to part of them and change them etc. without limitation) Also further enhancement may be achieved by reducing external inputs. In addition, in order to magnify a specific input other additional treatment can be provided, for example some antagonist to block and prevent the excitation of "opposite acting" receptors. For such use a device similar to FIG. 10 can be leveraged (other devices may serve as well) in the following manner: the device may be inserted into nasal cavity where a seal is conducted at the nasal valve. The nasal valve seal 7i is to be of having a collapsible area only at the top of it. The passageway 26i may be positioned at the inferior meatus (other meatuses may serve for it as well). The other passageway 26'i extends from passageway 26i towards the septum airway and upwards toward the olfactory region. The tail of passageway 26i includes a seal 7'i (illustrated in phantom), that block the access to all meatuses except for the superior meatus and the meatus in which the passageway 26i is positioned (inferior meatus in this specific example). This tails seal 7'i directs outgoing stream of air/signals/molecules etc to move out via passageway 26i or via the superior meatus and olfactory region. And from there they may continue out via the collapsible seal at the nasal valve. By that it promotes the reach of such signals/molecules/etc. to olfactory and enhances their effect. Passageway 26i and 26'i are connected via a membrane or "one directional" opens. Meaning that these opens are in a state of normally closed and have a small flange/part extending a bit into passageway 26i that are being opened due to outwards stream. Once opened outgoing stream of air/signals/molecule is directed to flow via passageway 26'i which directs it to olfactory. This enhances and promotes the reach of in-body signals to olfactory and may lead to magnify the effect of such signals. For example—molecules/odors/signals produced in mouth through eating and processing the food may reach olfactory via this channel and by that it may contribute to enhanced and more immediate response for the eaten food. Passageway 26'i may further comprise a treatment as relevant. In addition this specific embodiment prevents/reduces environmental incoming stream of air/signals/odors/molecules/etc. from reaching the olfactory, as this stream is directed to passageway 26i and bypasses olfactory. The prevention/reduction of signals/molecules etc. From outside from reaching the olfactory, leaves the olfactory and brain to act mainly according to the internal enhances signals, and to the treatment provided (if provided) via passageway 26'i. This mechanism may result in a significant therapeutic affect over body. For example: it is known that obese people tend to have higher level of leptin in plasma than lean (fat tissue produces leptin hormone). On the other hand obese people tend to response more strongly and to eat more due to smells of foods. This mechanism will allow them to avoid the smells of foods and related hunger and eating, while enhancing the intra-body signals affect and effect of the leptin—which was created by the body, in my opinion, at the first place, in order signal the brain a message of "satiation" and to stop/reduce eating. Meaning that by inhibiting smelling and blocks brain and hypothalamus' sensors from the relayed environmental chemical and by enhancing and enabling, internal body signals, we are manipulating olfactory and brain to be more dominated by internal signals and this may lead to enormous natural therapeutic effect. It is important to emphasize that by bringing signal to olfactory we may enhance, change and accelerate the response of the brain (and then body/mind etc.) to the signal. And this is due to the fast and direct connectivity of olfactory to hypothalamus and to amygdala and reward center.

Also it is easily understood that the apparatuses of this invention can be leveraged for prevention/manipulation/direction of internal body signals/molecule/etc. all or part/specific ones from olfactory or from other areas or to them, and affect the brain and body by that.

Such abilities of the device are currently almost impossible to do by other means. It can be leveraged for many treatments and may lead to an acute change in the regular cycles of the body and for efficient treatment or treatment aid.

Another non-limiting example for use of the devices of this invention would be to deliver smoking cessation air drug to olfactory. in this case the active ingredient maybe Chantix or other medication that can connect to and block nicotine receptors in olfactory organ and brain-to assist in smoking cessation, and to avoid the first digestive tract in the liver and digestive system that leads to side effects and to reduced effectiveness Example to another method would be: treating the maxillary sinus. Using nasal insert of embodiment 1 FIG. 1, having a seal 7 where these seals are collapsible allowing air/material flow outwards while preventing and directing inward flow to move only via the passageway 26. And having passageway 26 that reaches to and ends at maxillary sinus opening in the middle meatus directing treatment thereto. The device can be coated with adrenalin based material, for example Otrivin to shrink the nasal mucous and pain relief agent such as lidocaine. The TA would be the maxillary sinus and its opening. Inserting the nasal insert into the nasal cavity of the side of the required sinus to treat. Positioning seal 7 at the nasal opening while the passageway 26 is continuing into the nasal cavity and beyond the nasal valve and then into the middle meatus and towards the maxillary sinus opening (other path is passible as well). Then injecting a stream of saline water through the nasal insert 2 and directly to the nasal opening. This procedure can wash the sinus' opening, and the sinus itself and enable drainage of the sinus into nasal cavity and outside the nose. Afterwards this nasal insert is taken out and the user/patient should clean his nasal cavity by allowing the fluids to flow out blowing out, squeezing the nose etc. Alternatively a pump can be connected externally to nasal insert 2 while still located in the nasal cavity to drain the fluids. Another option would be to simply have the nasal device—possible in the internal surface 4 of the passageway 26 near the deepest part of it, containing an antibiotic medicine or other relevant treatment drug for the sinus. And having the user staying with the device sufficient amount of time allowing the device and airflow to direct the medicine to the sinus opening. The outgoing air will more easily travel via the other meatuses and through the collapsible sealing members out of the nose. Another option would be to use nasal insert 2 can to deliver a medication from an external source.

Another option would be to use a different type of nasal insert to deliver the medication—for example embodiments as depicted in FIG. 25 or 26 while having the thread/branch 9v or 9w reaching the middle meatus and the maxillary sinus opening. Another option would be using this embodiment while having the thread 9v or 9w made of absorbent material- to assist in drainage and cleaning of inflammation and related fluids and by that open the sinus opening.

Additional method would be to deliver medication to lungs while preventing it from the nasal cavity mucosa/ blood system/olfactory.

Furthermore the methods outlined above may also include wearing the nasal insert for a period of time, for example 12 hours, or 1 hour, or anything else with no limitation according to the treatment, and then taking it out for a period of time, for example 3 hours or other periods of time according to instructions, allowing the nose mucosa to recover, as well as for other reasons. After this period, the user may wear the nasal insert again for a period of time, remove it again for a period of time, and so on. Alternatively it can be used for few minutes/defined time/defined outcome/other sign to deliver the active ingredient and then removed until the next treatment. It can be also used to position a treatment and then removed while the treatment is continuously provided via a delayed slow release methods or other. In addition, in case of use of a re-usable nasal insert, the method also may include washing or cleaning the nasal insert prior to re-using it, and/or soaking it in odor/medication or re-filling it. In the case of a disposable nasal insert, the user may insert a new nasal insert for each use. The method may also include using the nasal insert continuously, or using the nasal insert only for selected periods of time.

The nasal inserts of the current invention meet the described above need of providing better and more efficient modes of drug and/or therapeutic agent delivery, through unique structure, materials and compatibility with nasal characteristics. In order to benefit the remedy that such nasal device may provide, a user will use the nasal device according to the specific treatment oriented instructions. As such, non-limiting embodiments of the present invention are directed to nasal devices coupled with specific instructions for a specific treatment of specific ailments. For example, in one non-limiting embodiment, a user may be asked to insert the relevant nasal device into one or both nasal cavities and to keep the nasal device inserted for a period of time according to instructions as dictated by the ailment that requires treatment. For instance, suitable time frames may include, but are not limited to, few minutes, few hours, or few days etc. Additionally, instructions may include a variety of steps and procedures for proper use of the nasal insert device, for example, but not limited to: inserting the nasal insert into one nostril and doing so while blocking the other nostril opening, or by inserting the nasal insert into one or both nostrils coupled with inhaling through the nostril and exhaling through the mouth, alternatively or in combination, by keeping the nasal device inserted overnight or for any other prolonged time periods.

It will be readily appreciated by those skilled in the art that modifications may be made to the invention without departing from the concepts disclosed in the foregoing description. Accordingly, the particular embodiments described in detail herein are illustrative only and are not limiting to the scope of the invention, which is to be given the full breadth of the appended claims and any and all equivalents thereof.

The claimed invention is:

1. A nasal insert for insertion into a nasal cavity comprising:
    a body comprising a proximal end configured to be positioned within the nasal cavity proximate to a nostril of the nasal cavity, at least one distal end configured to be positioned within the nasal cavity beyond a nasal valve proximate to a first region of the nasal cavity, and a sidewall extending between the proximal end and the at least one distal end, wherein the sidewall comprises an inner surface defining at least one passageway, an outer surface, and at least one opening through the sidewall, which is configured to be positioned within the nasal cavity; and
    at least one segment protruding from the sidewall of the body defining a branched passageway connected to the at least one passageway of the body, the at least one segment comprising a proximal end connected to the sidewall of the body about the at least one opening, a distal end configured to be positioned proximate to a second region of the nasal cavity beyond the nasal valve, and segment sidewall extending between the proximal end and the distal end of the segment,
    wherein the body and the at least one segment are configured to direct incoming or outgoing air and/or other components to reach a region(s) of the nasal cavity and/or beyond it, and/or to prevent the reach of incoming and/or outgoing air and/or other components from the region(s) in the nasal cavity and/or beyond it and/or to reduce an amount of air and/or other components in the region(s) or other region(s) of the nasal cavity and/or beyond it.

2. The nasal insert of claim 1, wherein the at least one passageway comprises a curved portion configured to extend from a nasal floor towards an olfactory region when the nasal insert is in the nasal cavity.

3. The nasal insert of claim 1, wherein the branched passageway of the at least one segment is substantially transverse to the at least one passageway of the body.

4. The nasal insert of claim 1, wherein the at least one passageway defined by the body comprises a first passageway portion configured to extend from the proximal end of the body to an end proximate to a nasal conchas, and a second passageway portion configured to extend from the first passageway portion to the at least one distal end of the body proximate to an olfactory region.

5. The nasal insert of claim 1, wherein the at least one passageway defined by the body of the nasal insert has a plurality of passageways beginning and/or terminating at a plurality of respective ends, wherein at least one of the plurality of passageways terminates proximate to an olfactory region and another of the plurality of passageways terminates proximate to another region of the nasal cavity.

6. The nasal insert of claim 1, wherein the body includes at least one seal extending directly or indirectly from an outer surface of a sidewall of the body configured to prevent air and/or other components from passing across the at least one seal, or wherein the at least one seal is a partial seal or a selective seal that reduces an amount or effect of the air and/or other components.

7. The nasal insert of claim 1, wherein the nasal insert comprises a material disposed on the body that is released from the body to produce a therapeutic effect.

8. The nasal insert of claim 1, further comprising at least one unitary thread-like element extending from the body, and a material disposed on the at least one unitary thread-like element and/or on the at least one passageway that is released from the at least one unitary thread-like element and/or from the at least one passageway to produce a therapeutic effect.

9. The nasal insert of claim 8, wherein the at least one unitary thread-like element is a longitudinally extending element that extends from the body, and wherein the at least one unitary thread-like element does not comprise a passageway therein.

10. The nasal insert of claim 8, wherein a plurality of the at least one unitary thread-like elements extend from the body.

11. The nasal insert of claim 1, further comprising at least one hook extending directly or indirectly from an outer surface of a sidewall of the body configured to hold the insert in the nasal cavity.

12. The nasal insert of claim 1, wherein at least one leaf-like element extends from the body, and wherein the at least one leaf-like element comprises a material disposed on the at least one leaf-like element that is released from the at least one leaf-like element to produce a therapeutic effect.

13. The nasal insert of claim 12, wherein the material that produces the therapeutic effect is released over time and/or in response to a trigger.

14. The nasal insert of claim 12, wherein the at least one leaf-like element is attached to the body of the nasal insert by at least one of a thread-like element, a string-like element, or a spring-like element, and wherein the material that produces the therapeutic effect is present on the at least one of the thread-like element, the string-like element, or the spring-like element, and wherein the material is released over time and/or in response to a trigger.

15. The nasal insert of claim 1, further comprising at least one valve in communication with the at least one passageway, and wherein the at least one valve permits air and/or other components in one direction in the at least one passageway.

16. The nasal insert of claim 15, wherein the at least one valve is defined in the body of the insert thereby permitting air and/or other components in one direction through the body.

17. The nasal insert of claim 1, further comprising at least one deflector extending from the body to deflect the flow of air and/or other components external to the at least one passageway.

18. The nasal insert of claim 1, further comprising
at least one flat leaf extending directly or indirectly from an outer surface of a sidewall of the body, wherein the body comprises a thread-like element.

19. The nasal insert of claim 1, wherein the body includes at least one seal extending directly or indirectly from an outer surface of a sidewall of the body and wherein the at least one seal is configured to coact with the nasal cavity to prevent air/components from passing across the at least one seal, or thereby reducing an amount or effect of the air and/or other components passing across the at least one seal, wherein the at least one seal may serve as a total seal, as a partial seal, or a selective seal.

20. The nasal insert of claim 1, wherein a sealing member or delivery element is attached to the body of the nasal insert by thread-like or string-like elements, wherein the nasal insert body is arranged to divide the nasal cavity to separated areas for treatment.

21. The nasal insert of claim 1, wherein the first region of the nasal cavity comprises one of the following regions of the nasal cavity: an inferior meatus, inferior concha, middle meatus, middle concha, superior meatus, superior concha, posterior meatus, upper concha, one or more of sinuses' opening, nasal roof, olfactory area, septum, septum opening, nasal mucosa, blood vessels trigeminal nerve, nasopharynx, or entrance to auditory tube, trachea, region(s), and
the second region of the nasal cavity comprises another of the following regions of the nasal cavity: inferior meatus, inferior concha, middle meatus, middle concha, superior meatus, superior concha, posterior meatus, upper concha, one or more of sinuses' opening, nasal roof, olfactory area, septum, septum opening, nasal mucosa, blood vessels trigeminal nerve, nasopharynx, or entrance to auditory tube, trachea, region(s).

22. The nasal insert of claim 1, wherein the first region of the nasal cavity comprises an inferior meatus or septum passageway of the nasal cavity and the second region of the nasal cavity comprises an olfactory region or roof of the nasal cavity.

23. The nasal insert of claim 1, further comprising at least one leaf-like element comprising a flat surface extending from the outer surface of the sidewall of the body.

24. The nasal insert of claim 23, wherein the at least one leaf-like element is configured to transition between a closed position for insertion of the nasal insert into the nasal cavity and an open position where the at least one leaf-like element leans against a septum or a concha(s) of the nasal cavity with a distal end of the leaf-like element positioned proximate to the second region of the nasal cavity.

25. The nasal insert of claim 23, wherein the at least one segment extends through the at least one leaf-like element.

26. The nasal insert of claim 1, wherein the at least one opening through the sidewall of the body is configured to be positioned beyond the nasal valve of the nasal cavity.

27. The nasal insert of claim 1, wherein the at least one passageway extends from the proximal end of the body to a plurality of distal ends of the body.

28. The nasal insert of claim 27, wherein the body is configured to allow incoming air and/or other components and/or discharging air and/or other components to pass through the proximal end and one or more of the plurality of distal ends of the body.

29. The nasal insert of claim 27, wherein at least one valve is provided within the at least one passageway so that the flow of air and/or other components is allowed in one direction through the at least one passageway.

30. The nasal insert of claim 27, wherein the body is configured to direct air and/or other components to flow to and/or from region(s) in the nasal cavity or beyond it.

31. The nasal insert of claim 27, wherein the body includes at least one seal extending directly or indirectly from an outer surface of a sidewall of the body configured to prevent air/components from passing across the at least one seal, or thereby reducing and/or changing an amount or effect of the air and/or other components passing across the at least one seal, wherein the at least one seal may serve as a total seal, as a partial seal, or a selective seal.

32. The nasal insert of claim 27, wherein the inner surface and/or the outer surface of the body and/or any layer in between, or any other part of the nasal insert comprises a material that is released from the body or the other parts of the nasal insert to produce a therapeutic effect to a user.

33. The nasal insert of claim 27, wherein at least one thread-like element extends from the body, wherein the at least one thread-like element comprises a material disposed on the at least one thread-like element that is released from the at least one thread-like element to produce a therapeutic effect to a user.

34. The nasal insert of claim 33, wherein the at least one thread-like element is a longitudinally extending element that extends from the body, and wherein the at least one thread-like element does not comprise a passageway therein.

35. The nasal insert of claim 33, wherein a plurality of thread-like elements extend from the body.

36. The nasal insert of claim 27, further comprising at least one hook extending directly or indirectly from an outer surface of a sidewall of the body that is configured to hold the nasal insert in place in the nasal cavity.

37. The nasal insert as claimed in claim 27, further comprising at least one valve in communication with the at least one passageway, wherein the at least one valve permits air and/or other components in one direction in the at least one passageway.

38. The nasal insert as claimed in claim 37, wherein the at least one valve is a flap that permits air and/or other components to proceed in one direction through the at least one passageway.

39. The nasal insert as claimed in claim 37, wherein the at least one valve is defined in the body of the insert and permits air and/or other components to proceed in one direction through the body.

40. The nasal insert as claimed in claim 37, wherein the at least one valve is in communication with the body and/or the at least one passageway and permits air and/or other components to fully, partially, or selectively, proceed through it.

41. The nasal insert of claim 27, further comprising:
at least one non-sealable deflector extending from the body to deflect the flow external to the at least one passageway.

42. The nasal insert of claim 1, further comprising:
at least one hook attached to and extending directly or indirectly from an outer surface of a sidewall of the body configured to hold the body in place in the nasal cavity; and
at least one flat leaf comprising a material disposed on the at least one flat leaf that is released from the at least one flat leaf to produce a therapeutic effect, wherein the at least one flat leaf extends directly or indirectly from an outer surface of a sidewall of the body, wherein the at least one flat leaf is not a seal.

43. The nasal cavity of claim 42, wherein the material disposed on the at least one flat leaf comprises a heat-sensitive/humidity sensitive, or other reactivity sensitive material that will dissipate over a period of time.

44. The nasal insert as claimed in claim 42, wherein the body further comprises at least one thread-like element extending from the body, and wherein the at least one thread-like element comprises the material that is released to produce the therapeutic effect, wherein the material is a heat-sensitive/humidity sensitive or other reactivity sensitive material that will dissipate over a period of time.

45. The nasal insert as claimed in claim 42, further comprising at least one deflector extending from the body to deflect flow across the body.

46. The nasal insert as claimed in claim 42, wherein the body includes the at least one passageway configured to direct flow over the at least one flat leaf.

47. The nasal insert of claim 27, wherein the body includes at least one seal extending directly or indirectly from an outer surface of a sidewall of the body and wherein the at least one seal is configured to coact with the nasal cavity to prevent air/components from passing across the at least one seal, or thereby reducing an amount or effect of the air and/or other components passing across the at least one seal, wherein the at least one seal may serve as a total seal, as a partial seal, or a selective seal.

48. A method for treating/assisting an ailment, or for other uses comprising the steps of:
inserting the body of the nasal insert of claim 1 into the nasal cavity, such that the at least one distal end of the body is proximate to the first region of the nasal cavity and the proximal end of the nasal insert is proximate to a nostril of the nasal cavity;
wherein the nasal insert body is configured to: (1) direct the air and/or any substance towards the first region, and/or towards other region(s) of the nasal cavity or beyond and/or to manipulate the air/any substance in relation to these regions; and/or (2) create a bypass of region(s) in the nasal cavity and/or beyond it; and/or (3) direct air/any substance away from region(s) in the nasal cavity and/or beyond it, thereby delaying, blocking, and/or reducing the amount of and/or manipulating the any substance from reaching or being in close proximity to region(s) of the nasal cavity or beyond; and/or (4) manipulate the first region, and/or other region(s) in the nasal cavity or beyond; and
wherein the direction of the any substance, and/or the blocking or reducing or manipulation of the any substance and/or the first region and/or other regions alters and/or diminishes bodily processes thereby producing a therapeutic or other effect.

* * * * *